United States Patent
Wehner et al.

(10) Patent No.: US 6,680,333 B2
(45) Date of Patent: Jan. 20, 2004

(54) IMIDAZOLIDINE DERIVATIVES, THEIR PREPARATION, THEIR USE AND PHARMACEUTICAL PREPARATIONS COMPRISING THEM

(75) Inventors: Volkmar Wehner, Sandberg (DE); Horst Blum, Frankfurt (DE); Hartmut Rütten, Idstein (DE); Hans Ulrich Stilz, Frankfurt (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 105 days.

(21) Appl. No.: 10/092,901

(22) Filed: Mar. 8, 2002

(65) Prior Publication Data

US 2003/0073723 A1 Apr. 17, 2003

(30) Foreign Application Priority Data

Mar. 10, 2001 (DE) .......................................... 101 11 877

(51) Int. Cl.⁷ ...................... A61K 31/44; A61K 31/415; C07D 401/14; C07D 233/40
(52) U.S. Cl. .................... 514/341; 514/389; 546/274.4; 548/319.5
(58) Field of Search ................................ 514/341, 389; 546/274.4; 548/319.5

(56) References Cited

U.S. PATENT DOCUMENTS

| | | |
|---|---|---|
| 5,389,614 A | 2/1995 | Konig et al. |
| 5,397,796 A | 3/1995 | Zoller et al. |
| 5,424,293 A | 6/1995 | Zoller et al. |
| 5,554,594 A | 9/1996 | Zoller et al. |
| 5,658,935 A | 8/1997 | Klingler et al. |
| 5,686,421 A | 11/1997 | Konig et al. |
| 5,939,556 A | 8/1999 | Zoller et al. |
| 5,981,492 A | 11/1999 | Zoller et al. |
| 5,998,447 A | 12/1999 | Stilz et al. |
| 6,034,238 A | 3/2000 | Wehner et al. |
| 6,218,415 B1 | 4/2001 | Wehner et al. |
| 6,331,552 B1 * | 12/2001 | Wehner et al. ............... 514/341 |
| 6,423,712 B1 | 7/2002 | Wehner et al. |

FOREIGN PATENT DOCUMENTS

| | | |
|---|---|---|
| EP | 0 796 855 | 3/1997 |
| EP | 0 842 943 | 11/1997 |
| EP | 0 842 944 | 11/1997 |
| EP | 0 842 945 | 11/1997 |
| EP | 0 903 353 A1 | 3/1999 |
| EP | 0 905 139 A2 | 3/1999 |
| EP | 0 918 059 A1 | 5/1999 |
| WO | WO 93/13798 | 7/1993 |
| WO | WO 93/15764 | 8/1993 |
| WO | WO 93/18057 | 9/1993 |
| WO | WO 94/15958 | 7/1994 |
| WO | WO 94/16094 | 7/1994 |
| WO | WO 94/17828 | 8/1994 |
| WO | WO 95/14008 | 5/1995 |
| WO | WO 95/15973 | 6/1995 |
| WO | WO 95/19790 | 7/1995 |
| WO | WO 96/00581 | 1/1996 |
| WO | WO 96/06108 | 2/1996 |
| WO | WO 96/20216 | 7/1996 |
| WO | WO 96/22966 | 8/1996 |
| WO | WO 96/33976 | 10/1996 |
| WO | WO 97/03094 | 1/1997 |
| WO | WO 98/04247 | 2/1998 |
| WO | WO 98/04913 | 2/1998 |
| WO | WO 98/42656 | 10/1998 |
| WO | WO 99/23063 | 5/1999 |
| WO | WO 99/24398 | 5/1999 |
| WO | WO 99/54321 | 10/1999 |
| WO | WO 99/60015 A1 | 11/1999 |
| WO | WO 00/00477 | 1/2000 |
| WO | WO 00/02903 | 1/2000 |
| WO | WO 00/69831 | * 11/2000 |

OTHER PUBLICATIONS

W. Duczek et al., "A Simple and Convenient Synthesis of N–Formly Amino Acid Esters Under Mild Conditions", Synthesis, Jan. 1996, pp. 37–38.

Wolfgang Steglich et al., "Eine einfache Synthese für N–Acylimine des Hexafluorund symm. Dichlortetrafluoracetons", Chem. Ber., 1974, pp. 1448–1498, No. 107.

(List continued on next page.)

Primary Examiner—D. Margaret Seaman
(74) Attorney, Agent, or Firm—Heller Ehrman White and McAuliffe

(57) ABSTRACT

The present invention relates to novel imidazolidine derivatives of formula I,

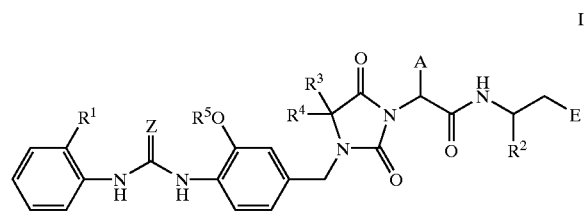

I wherein A, E, Z, $R^1$, $R^2$, $R^3$, $R^4$ and $R^5$ have the meanings indicated in the claims. The compounds of formula I are valuable pharmaceutical active compounds which are suitable, for example, for the treatment of inflammatory diseases, including rheumatoid arthritis, or allergic diseases. The compounds of formula I are inhibitors of the adhesion and migration of leukocytes and/or antagonists of the adhesion receptor VLA-4 belonging to the integrins group. They are generally suitable for the treatment of diseases which are caused by an undesired extent of leukocyte adhesion and/or leukocyte migration or are associated therewith or in which cell-cell or cell-matrix interactions which are based on the interactions of VLA-4 receptors with their ligands play a role. The invention furthermore relates to processes for the preparation of the compounds of formula I, their use and pharmaceutical preparations which contain compounds of formula I.

17 Claims, No Drawings

OTHER PUBLICATIONS

Abraham, William M. et al., "$\alpha_4$ – Integrins Mediate Antigen–induced Late Bronchial Responses and Prolonged Airway Hyperresponsiveness in Sheep", *J. Clin. Invest.*, vol. 93, Feb. 1994, 776–787, The American Society for Clinical Investigation, Inc., Ann Arbor, MI, USA.

Adams, David H. et al., "Experimental Graft Arteriosclerosis,", *Transplantation*, vol. 56, 794–799, No. 4, Oct., 1993, Lippincott Williams & Wilkins, Baltimore, MD, USA.

Albelda, Steven M. et al., "Molecular and Cellular Properties of PECAM–1 (endoCAM/CD31): A Novel Vascular Cell–Cell Adhesion Molecule", *The Journal Of Cell Biology*, vol. 114, No. 5, Sep. 1991, 1059–1068, The Rockefeller University Press, New York, NY, USA.

Barabadillo, Carmen et al., "Anti–integrin immunotherapy in rheumatoid arthritis: protective effect of anti–$\alpha^4$ antibody in adjuvant arthritis", *Springer Semin Immunopathol.*, (1995) 16:427–436, Springer–Verlag, New York, NY, USA.

Bergelson, J.M. et al., "Do integrins use a 'MIDAS touch'to grasp as Asp ?", *Current Biology*, 1995, vol. 5, No. 6, 615–617, Cell Press, Cambridge, MA, USA.

Bundgaard, Hans, "Novel chemical approaches in prodrug design", *Drugs Of The Future*, 1991, 16(5), 443–458, Prous Science, Philadelphia, PA, USA.

Cronstein, Bruce N. et al., "The adhesion molecules of inflammation", *Arthritis And Rheumatism*, vol. 36, No. 2, Feb. 1993, pp. 147–157.

Damle, Nitin K. et al., "Vascular cell adhesion molecule 1 induces T–cell antigen receptor–dependent activation of CD4 $^+$T lymphocytes", *PROC. NATL. ACAD. SCI. USA*, vol. 88, pp. 6403–6407, Aug. 1991, National Academy of Sciences, Washington DC, USA.

Dinther–Janssen, Anna C. H. M. Van et al., "The VLA–4/VCAM–1 pathway is involved in lymphocyte adhesion to endothelium in rheumatoid synovium [1]", *The Journal Of Immunology*, vol. 147, 4207–4210, No. 12, Dec. 5, 1991, The American Association of Immunologists, Bethesda, MD, USA.

Elices, Mariano J., "The integrin $\alpha4\beta1$ (VLA–4) as a therapeutic target", *Cell Adhesion And Human Disease*, 1995, Wiley, Chichester (Ciba Foundation Symposium 189) p. 79–90, John Wiley & Sons, Inc., Hoboken NJ, USA.

Elices, M. J. et al., "The integrin VLA–4 mediates leukocyte recruitment to skin inflammatory sites in vivo", *Clinical And Experimental Rheumatology*, 11, (Suppl. 8): S77–S80, 1993, Pisa, Italy.

Elices, Mariano J. et al., "Expression and Functional Significance of alternatively spliced CS1 fibronectin in rheumatoid arthritis microvasculature", *J. Clin. Invest.*, vol. 93, Jan. 1994, 405–416, The American Society for Clinical Investigation, Inc., Ann Arbor, MI, USA.

Elices, Mariano J. et al., "VCAM–1 on activated endothelium interacts with the leukocyte integrin VLA–4 at a site distinct from the VLA–4/Fibronectin binding site", *Cell*, vol. 60, 577–584, Feb. 23, 1990, Cell Press, Cambridge, MA, USA.

Fleisher, David et al., "Improved oral drug delivery: solubility limitations overcome by the use of prodrugs", *Advance Drug Delivery Reviews*, 19 (1996), 115–130, Elsevier Science B.V., Amsterdam, The Netherlands.

Foster, Carolyn A. Ph.D., "VCAM–1/$\alpha$4–integrin adhesion pathway: Therapeutic target for allergic inflammatory disorders", *J. Allergy Clin. Immunol.*, vol. 98, No. 6, Part 2, S270–S277, Mosby–Year Book, Inc, Oxford, UK.

Freedman, Arnold S., "Follicular Non–Hodgkin's lymphoma cell adhesion to normal germinal centers and neoplastic follicles involves very late antigen–r and vascular cell adhesion molecule–1", *Blood*, vol. 79, No. 1 (Jan. 1), 1992: pp. 206–212, Birmingham, AL USA.

Goldschmidt, Von Stefan et al, "Über Peptid–Synthesen I", *Org. Chem. Institut der Technischen Hochschule*, pp. 217–231, Nov. 30, 1951, München, Germany.

Harlan, John M., "Leukocyte–Endothelial Interactions", *Blood*, vol. 65, No. 3 (Mar.), 1985: pp 513–525, Birmingham, AL USA.

Isobe, M. et al., "Effect of Anti–VCAM–1 and Anti–VLA–4 Monoclonal Antibodies on Cardiac Allograft Survival and Response to Soluble Antigens in Mice", *Transplantation Proceedings*, vol. 26, No. 2 (Apr.), 1994: pp. 867–868, Elsevier Science, Inc., New York, NY, USA.

Issekutz, Thomas B., "Inhibition of in vivo lymphocyte migration to inflammation and homing to lymphoid tissues by the TA–2 monoclonal antibody —a likely role for VLA–4 in vivo", *The Journal Of Immunology*, vol. 147, No. 12, Dec. 15, 1991, 4178–4184, The American Association of Immunologists, Bethesda, MD, USA.

Issekutz, Thomas B. et al., "Rat Blood Neutrophils Express Very Late Antigen 4 and it Mediates Migration to Arthritic Joint and Dermal Inflammation", *J. EXP. MED.*, vol. 183, May 1996, 2174–2184, The Rockefeller University Press, New York NY USA.

Kilger, G et al., "Molecular analysis of the physiological and pathophysiological role of $\alpha_4$ –integrins", *J. MOL. MED.*, (1995) 73:347–354, Springer–Verlag, New York NY USA.

Kuijpers, Taco W., "Pathophysiological aspects of VLA–4 interactions and possibilities for therapeutical interventions", *Springer Semin Immunopathol.*, (1995) 16:379–389, Spring–Verlag, New York NY USA.

Laffon, Armando et al., "Upregulated Expression and Function of VLA–4 Fibronectin Receptors on Human Activated T Cells in Rheumatoid Arthritis", *J. Clin. Invest.*, vol. 88, August 1991, 546–552, The American Society for Clinical Investigation, Inc., Ann Arbor, MI USA.

McMurray, Robert W., "Adhesion Molecules in Autoimmune Disease", *Seminars In Arthritis And Rheumatism*, vol. 25, No. 4 (Feb.), 1996: pp. 215–233, Elsevier Science USA, New York, NY USA.

Metzger, W. James, "Therapeutic approaches to asthma based on VLA–4 integrin and its counter receptor", *Springer Semin Immunopathol.*(1995) 16:467–478, Springer–Verlag, New York NY USA.

Molossi, Silvana, et al., "Blockade of Very Late Antigen–4 Intergrin Binding to Fibronectin with Connecting Segment–1 Peptide Reduces Accelerated Coronary Arteriopathy in Rabbit Cardiac Allografts", *J. Clin Invest.*, vol. 95, Jun. 1995, 2601–2610, The American Society for Clinical Investigation, Inc., Ann Arbor MI USA.

Morales–Ducret, Jeanette, "$\alpha_4$ / $\beta_1$ Integrin (VLA–4) Ligands in Arthritis —Vascular Cell Adhesion Molecule–1 Expression in Synovium and on Fibroblast–Like Synoviocytes [1]", *The Journal Of Immunology*, vol. 149, No. 4, Aug. 15, 1992, 1424–1431, The American Association of Immunologists, Bethesda, MD, USA.

Muacevic, G., "New Apparatus and Method for the toxicological investigation of Metered Aerosols in Rats", *Arch. Toxicol.*, 34 1–8 (1975), Springer–Verlag, New York NY USA.

O'Brien, Kevin D. et al., "Vascular Cell Adhesion Molecule–1 is Expressed in Human Coronary Atherosclerotic Plaques", *J. Clin. Invest.*, vol. 92, Aug. 1993, 945–951, The American Society for Clinical Investigation, Inc., Ann Arbor MI USA.

Ockenhouse, Christian F. et al., Human Vascular Endothelial Cell Adhesion Receptors for *Plasmodium falciparum*–infected Erythrocytes: Roles for Endothelial Leukocyte Adhesion Molecule 1 and Vascular Cell Adhesion Molecule 1, *The Journal Of Experimental Medicine*, vol. 176, Oct. 1992, 1183–1189, Rockefeller University Press, New York NY USA.

Osborn, Laurelee, et al., "Direct Expression Cloning of Vascular Cell Adhesion Molecule 1, a Cytokin–Induced Endothelial Protein that Binds to Lymphocytes", *Cell* vol. 59, 12–3 =1211, Dec. 22, 1989, Cell Press, Cambridge MA USA.

Osborn, Laurelee, "Leukocyte Adhesion to Endothelium in Inflammation", *Cell*, vol. 62, 3–6, Jul. 13, 1980, Cell Press, Cambridge MA USA.

Postigo, Antonio A. et al., "Increased Binding of Synovial T Lymphocytes from Rheumatoid Arthritis to Endothelial–Leukocyte Adhesion Molecule–1 (ELAM–1) and Vascular Cell Adhesion Molecule–1 (VCAM–1)", *J. Clin. Invest.*, vol. 89, May 1992, 1445–1452, The American Society for Clinical Investigation, Inc., Ann Arbor MI USA.

Poon, B.Y. et al., "Emigrated Neutrophils Regulate Ventricular Contractility via $\alpha_4$Integrin", American Heart Association, Inc., *Lippincott Williams & Wilkins*, Baltimore MD USA.

Renkonen, Risto et al., "Rapid Communication: Expression of Endothelial Adhesion Molecules in Vivo: *Increased Endothelial ICAM–2 Expression in Lymphoid Malignancies*" American Journal Of Pathology, vol. 140, No. 4, Apr. 1992, 763–767.

Rice, G. Edgar et al., "An Inducible Endothelial Cell Surface Glycoprotein Mediates Melanoma Adhesion", *Science*, vol. 246, Dec. 8, 1989, 1303–1306, American Association for the Advancement of Science, Stanford University's High Wire Press, Palo Alto CA USA.

Rico, Joseph G. et al., "A Highly Stereoselective Michael Addition to an $\alpha$, $\beta$–Unsaturated Ester as the Crucial Step in the Synthesis of a Novel $\beta$–Amino Acid–Containing Fibrinogen Receptor Antagonist", *J. Org. Chem.*, 1993, 58, 7948–7951, American Chemical Society, Washington DC USA.

Ruoslahti, Erkki, "Fibronectin and its receptors", *Ann. Rev. Biochem.*, 1988, 57:375–413, Annual Reviews Inc. Palo Alto CA USA.

Seiffge, D. et al., "Effects of Different Mediators or Cytokines and Monoclonal Antibodies to Adhesion Molecules on Leukocyte Adhesion in Rat Mesenteric Venules", *Int. J. Microcirc.*, 1995, 15, 301–308, S. Karger AG, Basel Switzerland.

Shih, Peggy T. et al., "Blocking Very Late Antigen–4 Integrin Decrease Leukocyte Entry and Fatty Streak Formation in Mice Fed an Atherogenic Diet", American Heart Association, Inc., *Lippincott Williams & Wilkins*, Baltimore MD USA.

Springer, Timothy A., "Traffic Signals for Lymphocyte Recirculation and Leukocyte Emigration: The Multistep Paradigm", *Cell* vol. 76, 301–314, Jan. 28, 1994, Cell Press, Cambridge MA USA.

Stoolman, Lloyd M., "Adhesion Molecules Controlling Lymphocyte Migration", *Cell*, vol. 56, 907–910, Mar. 24, 1989, Cell Press, Cambridge MA USA.

Takeuchi, Tsutomu et al., "Upregulated Expression and Function of Integrin Adhesion Receptors in Systemic Lupus Erythematosus Patients with Vasculitis", *J. Clin. Invest.*, vol. 92, Dec. 1993, 3008–3016, The American Society for Clinical Investigation, Inc., Ann Arbor MI USA.

Tropp, Casper, "Einwirkung von Phosgen auf polypeptid–artige Derivate der p–Amino–benzoesäure. Bildung von 1.3–substituierten Hydantoinen", Apr. 16, 1928, 1431–1439.

Yang, Xiao–Dong et al., "Inhibition of insulitis and prevention of diabetes in nonobese diabetic mice by blocking L–selectin and very late antigen 4 adhesion receptors", *Proc. Natl. Acad. Sci. USA.*, vol. 90, pp. 10494–10498, Nov. 1993, National Academy of Sciences, Washington DC, USA.

Yednock, Ted A., "Prevention of experimental autoimmune encephalomyelitis by antibodies against $\alpha 4$ $\beta 1$ integrin", *Nature*, vol. 356, Mar. 5, 1992, pp. 63–66, Stanford CA USA.

Zettlmeissl, Gerd et al., "Expression and Characterization of Human CD4: Immunoglobulin Fusion Proteins", *Dna And Cell Biology*, vol. 9, No. 5, 1990, pp. 347–353, Mary Ann Liebert, Inc., Publishers, Larchmont NY USA.

\* cited by examiner

IMIDAZOLIDINE DERIVATIVES, THEIR PREPARATION, THEIR USE AND PHARMACEUTICAL PREPARATIONS COMPRISING THEM

This application claims priority to German Patent Application 10111877.5, filed Mar. 10, 2001, which is hereby incorporated by reference, in their entirety. All references cited below, including patents, patent applications and scientific journals and books also are herein incorporated by reference in their entirety.

BACKGROUND OF THE INVENTION

1. Field of Invention

This invention relates to novel imidazolidine derivatives, their preparation, their use and pharmaceutical preparations comprising them.

2. Description of Related Art

The integrins are a group of adhesion receptors, which play an important role in cell-cell-binding and cell-extracellular matrix-binding processes. They have an αβ-heterodimeric structure and exhibit a wide cellular distribution and a high extent of evolutive conservation. The integrins include, for example, the fibrinogen receptor on platelets, which interacts especially with the RGD sequence of fibrinogen, or the vitronectin receptor on osteoclasts, which interacts especially with the RGD sequence of vitronectin or of osteopontin. The integrins are divided into three major groups, the β2 subfamily containing the representatives LFA-1, Mac-1 and p150/95, which are responsible in particular for cell-cell interactions of the immune system, and the subfamilies β1 and β3, whose representatives mainly mediate cell adhesion to components of the extracellular matrix (Ruoslahti, Annu. Rev. Biochem., 57:375 (1988)). The integrins of the β1 subfamily, also called VLA proteins (very late (activation) antigen), include at least six receptors, which interact specifically with fibronectin, collagen and/or laminin as ligands. Within the VLA family, the integrin VLA-4 (α4β1) is atypical insofar as it is mainly restricted to lymphoid and myeloid cells and is responsible in these for cell-cell interactions with a large number of other cells. VLA-4 mediates, for example, the interactions of T and B lymphocytes with the heparin II-binding fragment of human plasma fibronectin (FN). The binding of VLA-4 with the heparin II-binding fragment of the plasma fibronectin is based especially on an interaction with an LDVP sequence. In contrast to the fibrinogen or vitronectin receptor, VLA-4 is not a typical RGD-binding integrin (Kilger and Holzmann, J. Mol. Meth., 73:347 (1995)).

The leukocytes circulating in the blood normally exhibit only a low affinity for the vascular endothelial cells, which line the blood vessels. Cytokines, which are released from inflamed tissue, cause the activation of endothelial cells and thus, the expression of a large number of cell surface antigens. These include, for example, the adhesion molecules ELAM-1 (endothelial cell adhesion molecule-1; also designated as E-selectin), which, inter alia, binds neutrophils, ICAM-1 (intercellular adhesion molecule-1), which interacts with LFA-1 (leukocyte function-associated antigen 1) on leukocytes, and VCAM-1 (vascular cell adhesion molecule-1), which binds various leukocytes, inter alia lymphocytes (Osborn et al., Cell, 59:1203 (1989)). VCAM-1 is, like ICAM-1, a member of the immunoglobulin gene superfamily. VCAM-1 (first known as INCAM-110) was identified as an adhesion molecule, which is induced on endothelial cells by inflammatory cytokines, such as TNF and IL-1 and lipopolysaccharides (LPS). Elices et al., Cell, 60:577 (1990) showed that VLA-4 and VCAM-1 form a receptor-ligand pair which mediates the attachment of lymphocytes to activated endothelium. The binding of VCAM-1 to VLA-4 does not take place due to an interaction of the VLA-4 with an RGD sequence, such a sequence is not contained in VCAM-1 (Bergelson et al., Current Biology, 5:615 (1995)). In addition, VLA-4 occurs, however, on other leukocytes, and the adhesion of leukocytes other than lymphocytes is also mediated via the VCAM-1/VLA-4 adhesion mechanism. VLA-4 thus represents an individual example of a β1-integrin receptor which, via the ligands VCAM-1 and fibronectin, plays an important role both in cell-cell interactions and in cell-extracellular matrix interactions.

The cytokine-induced adhesion molecules play an important role in the recruitment of leukocytes into extravascular tissue regions. Leukocytes are recruited into inflammatory tissue regions by cell adhesion molecules, which are expressed on the surface of endothelial cells, and serve as ligands for leukocyte cell surface proteins or protein complexes (receptors) (the terms ligand and receptor also can be used vice versa). Leukocytes from blood must first adhere to endothelial cells before they can migrate into the synovium. Since VCAM-1 binds to cells, which carry the integrin VLA-4 (α4β1), such as eosinophils, T and B lymphocytes, monocytes or neutrophils, it and the VCAM-1/VLA-4 mechanism have the function of recruiting cells of this type from the bloodstream into areas of infection and inflammatory foci (Elices et al., Cell, 60:577 (1990); Osborn, Cell, 62:3 (1990); Issekutz et al., J. Exp. Med., 183:2175 (1996)).

The VCAM-1/VLA-4 adhesion mechanism has been connected with a number of physiological and pathological processes. Apart from by cytokine-induced endothelium, VCAM-1 is additionally expressed, inter alia, by the following cells: myoblasts, lymphoid dendritic cells and tissue macrophages, rheumatoid synovium, cytokine-stimulated neural cells, parietal epithelial cells of Bowman's capsule, the renal tubular epithelium, inflamed tissue during heart and kidney transplant rejection, and by intestinal tissue in graft versus host disease. VCAM-1 is also found to be expressed on those tissue areas of the arterial endothelium, which correspond to early atherosclerotic plaques of a rabbit model. In addition, VCAM-1 is expressed on follicular dendritic cells of human lymph nodes and is found on stroma cells of the bone marrow, for example in the mouse. The latter finding points to a function of VCAM-1 in B-cell development. Apart from on cells of hematopoetic origin, VLA-4 is also found, for example, on melanoma cell lines, and the VCAM-1/VLA-4 adhesion mechanism is connected with the metastasis of such tumors (Rice et al., Science, 246:1303 (1989)).

The main form, wherein VCAM-1 occurs in vivo on endothelial cells and which is the dominant form in vivo is designated as VCAM-7D and carries seven immunoglobulin domains. The domains 4, 5 and 6 are similar in their amino acid sequences to the domains 1, 2 and 3. In a further form consisting of six domains, designated here as VCAM-6D, the fourth domain is removed by alternative splicing. VCAM-6D can also bind VLA-4-expressing cells.

Further details concerning VLA-4, VCAM-1, integrins and adhesion proteins are found, for example, in the articles by Kilger and Holzmann, J. Mol. Meth., 73:347 (1995); Elices, Cell Adhesion in Human Disease, Wiley, Chichester 1995, p. 79; Kuijpers, Springer Semin. Immunopathol., 16:379 (1995).

On account of the role of the VCAM-1/VLA-4 mechanism in cell adhesion processes, which are of importance, for example, in infections, inflammation or atherosclerosis, it has been attempted by means of interventions in these adhesion processes to control disorders, in particular, for example, inflammations (Osborn et al., *Cell,* 59:1203 (1989)). A method of doing this is the use of monoclonal antibodies which are directed against VLA-4. Monoclonal antibodies (mABs) of this type, which as VLA-4 antagonists block the interaction between VCAM-1 and VLA-4, are known. Thus, for example, the anti-VLA-4 mABs HP2/1 and HP1/3 inhibit the attachment of VLA-4-expressing Ramos cells (B-cell-like cells) to human umbilical cord endothelial cells and to VCAM-1-transfected COS cells. Likewise, the anti-VCAM-1 mAB 4B9 inhibits the adhesion of Ramos cells, Jurkat cells (T-cell-like cells) and HL60 cells (granulocyte-like cells) to COS cells transfected with genetic constructs which cause VCAM-6D and VCAM-7D to be expressed. In vitro data with antibodies which are directed against the α4 subunit of VLA-4 show that the adhesion of lymphocytes to synovial endothelial cells is blocked, an adhesion which plays a role in rheumatoid arthritis (van Dinther-Janssen et al., *J. Immunol.,* 147:4207 (1991)).

In vivo experiments have shown that experimental autoimmune encephalomyelitis can be inhibited by anti-α4 mAB. The migration of leukocytes into an inflammatory focus is likewise blocked by a monoclonal antibody against the α4 chain of VLA-4. The influencing of the VLA-4-dependent adhesion mechanism using antibodies has also been investigated in an asthma model in order to investigate the role of VLA-4 in the recruitment of leukocytes into inflamed lung tissue (WO-A-93/13798). The administration of anti-VLA-4 antibodies inhibited the late-phase reaction and the airway hyperreaction in allergic sheep. The importance of VLA-4 as a target for the treatment of asthma is discussed in detail in Metzger, *Springer Semin. Immunopathol.,* 16:467 (1995).

The VLA-4-dependent cell adhesion mechanism was also investigated in a primate model of inflammatory bowel disease (IBD). In this model, which corresponds to ulcerative colitis in man, the administration of anti-α4 antibodies resulted in a significant reduction of the acute inflammation.

Moreover, it was possible to show that the VLA-4-dependent cell adhesion plays a role in the following clinical conditions including the following chronic inflammatory processes: rheumatoid arthritis (Cronstein and Weismann, *Arthritis Rheum.,* 36:147 (1993); Elices et al., *J. Clin. Invest.,* 93:405 (1994)), diabetes mellitus (Yang et al., *Proc. Natl. Acad. Sci. USA,* 90:10494 (1993), systemic lupus erythematosus (Takeuchi et al., *J. Clin. Invest.,* 92:3008 (1993)), allergies of the delayed type (type IV allergy) (Elices et al., *Clin. Exp. Rheumatol.,* 11:S77 (1993)), multiple sclerosis (Yednock et al., *Nature,* 356:63 (1992)), malaria (Ockenhouse et al., *J. Exp. Med.,* 176:1183 (1992)), atherosclerosis (O'Brien et al., *J. Clin. Invest.,* 92:945 (1993); Shih et al., *Circ. Res.,* 84:345 (1999)), transplantation (Isobe et al., *Transplantation Proceedings,* 26:867 (1994)), various malignancies, for example melanoma (Renkonen et al., *Am. J. Pathol.,* 140:763 (1992)), lymphoma (Freedman et al., *Blood,* 79:206 (1992)) and others (Albelda et al., *J. Cell Biol.,* 114:1059 (1991)).

The interaction of VLA-4 with VCAM-1 and fibronectin is connected with some pathophysiological processes in cardiovascular diseases. In an in vitro cell system, infiltrated neutrophils inhibit the cell contraction (negative inotropy) of cardiomyocytes by 35%. It was possible to inhibit this negative inotropic action of neutrophils by an anti-α4 antibody, but not by an anti-CD 18 antibody (Poon et al., *Circ. Res.,* 84:1245 (1999)). The importance of VLA-4 in the pathogenesis of atherosclerosis was shown in a mouse model of atherosclerosis. Thus, the CS-1 peptide, which is directed against the binding site of VLA-4 on fibronectin, inhibits the recruitment of leukocytes and the accumulation of fat in the aorta and thus, the formation of atherosclerotic plaques in atherogenically fed LDL receptor knockout mice (Shih et al., *Circ. Res.,* 84:345 (1999)). Using the same CS-1 peptide, it was furthermore possible to show in a heterotopic heart transplantation model in the rabbit that the formation of a transplant vasculopathy can be significantly decreased by the blockade of the interaction of VLA-4 and fibronectin (Molossi et al., *J. Clin. Invest.,* 95:2601 (1995)).

Blocking of VLA-4 by suitable antagonists, thus, offers effective therapeutic possibilities of treating, for example, in particular various inflammatory conditions including asthma and IBD. The particular relevance of VLA-4 antagonists for the treatment of rheumatoid arthritis results here, as already stated, from the fact that leukocytes from the blood must first adhere to endothelial cells before they can migrate into the synovium, and that the VLA-4 receptor plays a role in this adhesion. The fact that VCAM-1 is induced on endothelial cells by inflammatory agents (Osborn, *Cell,* 62:3 (1990); Stoolman, *Cell,* 56:907 (1989)), and the recruitment of various leukocytes into areas of infection and inflammatory foci has already been discussed above. T cells adhere to activated endothelium here mainly via the LFA-1/ICAM-1 and VLA-4/VCAM-1 adhesion mechanisms (Springer, *Cell,* 76:301 (1994)). On most synovial T cells, the binding capacity of VLA-4 for VCAM-1 is increased in rheumatoid arthritis (Postigo et al., *J. Clin. Invest.,* 89:1445 (1992)). In addition, an increased adhesion of synovial T cells to fibronectin has been observed (Laffon et al., *J. Clin. Invest.,* 88:546 (1991); Morales-Ducret et al., *J. Immunol.,* 149:1424 (1992)). Thus, VLA-4 is upregulated both with respect to its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective disease prevention was observed (Barbadillo et al., *Springer Semin. Immunopathol.,* 16:427 (1995)). CS-1 peptidomimetics, which contain an aspartic acid unit or a derivative thereof in the molecule and which inhibit the binding of VLA-4 to the CS-1 sequence of the matrix protein fibronectin, are described in WO-A-00/02903. Thus, VLA-4 is an important therapeutic target molecule.

The abovementioned VLA-4 antibodies and the use of antibodies as VLA-4 antagonists are described in the patent applications WO-A-93/13798, WO-A-93/15764, WO-A-94/16094, WO-A-94/17828 and WO-A-95/19790. The patent applications WO-A-94/15958, WO-A-95/15973, WO-A-96/00581, WO-A-96/06108 and WO-A-96/20216 describe peptide compounds as VLA4 antagonists. The use of antibodies and peptide compounds as pharmaceuticals, however, is afflicted with disadvantages, such as, for example, lack of oral availability, easy degradability or immunogenic action on long-term administration, and thus, there is a need for VLA-4 antagonists having a favorable property profile for use in the therapy and prophylaxis of various disease conditions.

WO-A-95/14008, WO-A-93/18057, U.S. Pat. Nos. 5,658, 935, 5,686,421, 5,389,614, 5,397,796, 5,424,293 and 5,554, 594 describe substituted 5-membered ring heterocycles, which have an amino, amidino or guanidino function at the N-terminal end of the molecule and which show platelet aggregation-inhibiting actions. EP-A-796 855 further describes heterocycles, which are inhibitors of bone resorption. EP-A-842 943, EP-A-842 945 and EP-A-842 944 describe compounds from these series and further compounds that surprisingly inhibit leukocyte adhesion and are VLA-4 antagonists. EP-A-903 353, EP-A-905 139, EP-A-918 059, U.S. Pat. Nos. 6,034,238, 6,331,552 B, WO-99/23063, WO-A-99/24398, WO-A-99/54321 and WO-A-99/60015 further describe compounds which inhibit leukocyte adhesion and are VLA-4-antagonists. The properties of these compounds, however, are still not satisfactory in various respects and there is a need for compounds having a further improved property profile. EP-A-918 059 and U.S. Pat. No. 6,331,552 B mentions, inter alia, imidazolidine derivatives, wherein the imidazolidine ring is bonded via its 1-position to the carbon atom in the 2-position of a 2-(cycloalkylalkyl) acetylamino unit or a 2-isobutylacetylamino unit. Not specifically disclosed, however, are the imidazolidine derivatives of formula I of the present invention, which are distinguished by their advantageous property profile and in particular by their markedly increased potency.

2. SUMMARY OF THE INVENTION

The present invention relates to a compound of formula I,

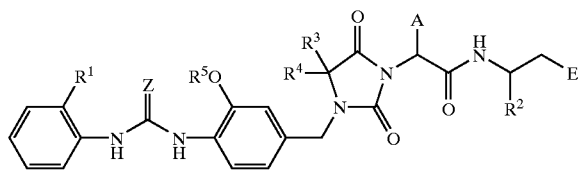

wherein
A is cyclopropylmethyl- or isobutyl;
E is —CO—$R^6$, —CO—H or —$CH_2$—O—$R^7$;
Z is oxygen or sulfur;
$R^1$ is hydrogen or methyl;
$R^2$ is phenyl, pyridyl or ($C_1$–$C_4$)-alkyl, where the alkyl residue can be substituted by one or more fluorine atoms and the phenyl residue can be substituted by one or more identical or different substituents selected from the group consisting of ($C_1$–$C_4$)-alkyl, ($C_1$–$C_4$)-alkoxy, methylenedioxy, ethylenedioxy, halogen, trifluoromethyl and trifluoromethoxy;
$R^3$ and $R^4$ are methyl or trifluoromethyl;
$R^5$ is hydrogen or ($C_1$–$C_4$)-alkyl, where the alkyl residue can be substituted by one or more fluorine atoms;
$R^6$ is hydroxyl, ($C_1$–$C_{10}$)-alkoxy, phenyl-($C_1$–$C_8$)-alkoxy, phenyloxy, ($C_1$–$C_8$)-alkylcarbonyloxy-($C_1$–$C_6$)-alkoxy, phenylcarbonyloxy-($C_1$–$C_6$)-alkoxy, phenyl-($C_1$–$C_6$)-alkylcarbonyloxy-($C_1$–$C_6$)-alkoxy, ($C_1$–$C_8$)-alkoxycarbonyloxy-($C_1$–$C_6$)-alkoxy, phenyloxycarbonyloxy-($C_1$–$C_6$)-alkoxy, phenyl-($C_1$–$C_6$)-alkoxycarbonyloxy-($C_1$–$C_6$)-alkoxy, amino, mono(($C_1$–$C_{10}$)-alkyl)amino or di(($C_1$–$C_{10}$)-alkyl) amino;
$R^7$ is hydrogen or ($C_1$–$C_4$)-alkyl;
in all its stereoisomeric forms and mixtures thereof in all ratios,
or its physiologically acceptable salts.

The present invention also relates to a process for the preparation of compounds of formula I, which comprises reacting a compound of formula II with a compound of formula III

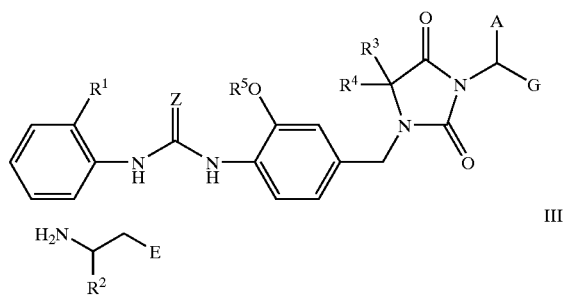

where A, E, Z, $R^1$, $R^2$, $R^3$, $R^4$ and $R^5$ are as defined in formula I or functional groups are present in protected form or in the form of precursors, and where G is hydroxycarbonyl, ($C_1$–$C_6$)-alkoxycarbonyl or activated carboxylic acid derivatives.

The present invention further embodies pharmaceutical compositions, which comprise one or more compounds of formula I and/or derivatives thereof and/or physiologically acceptable salts thereof and a pharmaceutical acceptable carrier.

The present invention also relates to methods of treating, for example, inflammation, arthritis, rheumatoid arthritis, polyarthritis, inflammatory bowel disease, systemic lupus erythematosus, multiple sclerosis, inflammatory diseases of the central nervous system, asthma, allergies, cardiovascular diseases, atherosclerosis, myocardial infarct, the acute coronary syndrome, stroke, restenoses, diabetes, damage to organ transplants, immune diseases, autoimmune diseases, tumor growth, tumor metastasis, or malaria comprising administering to a mammal in need thereof a effective amount of a compound of formula I, or a derivative thereof, or a pharmaceutically acceptable salt thereof.

The present invention further relates to a method for cardioprotection or secondary prophylaxis of stroke, and a method of inhibiting the adhesion and/or migration of leukocytes, or inhibiting the VLA-4 receptor comprising administering to a mammal in need thereof a effective amount of a compound of formula I, or a derivative thereof, or a pharmaceutically acceptable salt thereof.

3. DETAILED DESCRIPTION OF THE PREFERRED EMBODIMENTS

The present invention relates to compounds of formula I,

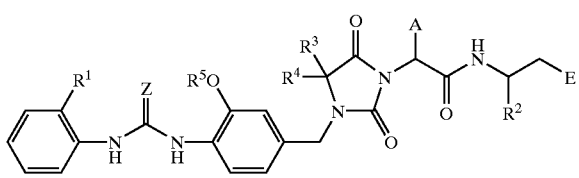

wherein
A is cyclopropylmethyl- or isobutyl;
E is —CO—$R^6$, —CO—H or —$CH_2$—O—$R^7$;
Z is oxygen or sulfur;
$R^1$ is hydrogen or methyl;
$R^2$ is phenyl, pyridyl or ($C_1$–$C_4$)-alkyl, where the alkyl residue can be substituted by one or more fluorine atoms and the phenyl residue can be substituted by one or more identical or different substituents selected from the group consisting of $(C_1–C_4)$-alkyl, $(C_1–C_4)$-alkoxy, methylenedioxy, ethylenedioxy, halogen, trifluoromethyl and trifluoromethoxy;

$R^3$ and $R^4$ are methyl or trifluoromethyl;

$R^5$ is hydrogen or $(C_1–C_4)$-alkyl, where the alkyl residue can be substituted by one or more fluorine atoms;

$R^6$ is hydroxyl, $(C_1–C_{10})$-alkoxy, phenyl-$(C_1–C_8)$-alkoxy, phenyloxy, $(C_1–C_8)$-alkylcarbonyloxy-$(C_1–C_6)$-alkoxy, phenylcarbonyloxy-$(C_1–C_6)$-alkoxy, phenyl-$(C_1–C_6)$-alkylcarbonyloxy-$(C_1–C_6)$-alkoxy, $(C_1–C_8)$-alkoxycarbonyloxy-$(C_1–C_6)$-alkoxy, phenyloxycarbonyloxy-$(C_1–C_6)$-alkoxy, phenyl-$(C_1–C_6)$-alkoxycarbonyloxy-$(C_1–C_6)$-alkoxy, amino, mono$((C_1–C_{10})$-alkyl)amino or di$((C_1–C_{10})$-alkyl)amino;

$R^7$ is hydrogen or $(C_1–C_4)$-alkyl;

in all their stereoisomeric forms and mixtures thereof in all ratios, and their physiologically acceptable salts.

Alkyl residues can be straight-chain or branched, whether they carry substituents or occur as substituents of other residues, for example, in fluoroalkyl residues, alkoxy residues or alkoxycarbonyl residues. Alkyl residues include, for example, methyl, ethyl, n-propyl, isopropyl (=1-methylethyl=$iC_3H_7$), n-butyl, isobutyl (=2-methylpropyl), sec-butyl (=1-methylpropyl), tert-butyl (=1,1-dimethylethyl), n-pentyl, isopentyl, tert-pentyl, neopentyl, n-hexyl, 3-methylpentyl, isohexyl, neohexyl, n-heptyl, 2,3,5-trimethylhexyl, n-octyl, n-nonyl, or n-decyl. Preferred alkyl residues are selected from the group consisting of methyl, ethyl, n-propyl, isopropyl, n-butyl, isobutyl, sec-butyl, and tert-butyl. In alkyl residues, one or more, (e.g., 1, 2, 3, 4 or 5), hydrogen atoms can be substituted by fluorine atoms. Examples of such fluoroalkyl residues are trifluoromethyl, 2,2,2-trifluoroethyl, pentafluoroethyl, heptafluoroisopropyl. Substituted alkyl residues, for example phenylalkyl residues or fluoroalkyl residues, can be substituted in any desired positions.

Phenyl residues can be unsubstituted or mono- or polysubstituted (e.g. mono-, di-, tri-, tetra- or pentasubstituted) by identical or different substituents. Preferably, a phenyl residue carries one or two identical or different substituents, if it is substituted. This also applies to substituted phenyl residues in groups, such as phenylalkyl, phenylcarbonyl, and other substituted phenyl residues described herein. Phenylalkyl residues are, for example, benzyl, 1-phenylethyl or 2-phenylethyl, and preferably benzyl, all of which also can be substituted.

In monosubstituted phenyl residues, the substituent can be substituted in the 2-position, the 3-position or the 4-position. Disubstituted phenyl residues can be substituted in the 2,3-position, 2,4-position, 2,5-position, 2,6-position, 3,4-position or 3,5-position. In trisubstituted phenyl residues, the substituents can be substituted in the 2,3,4-position, 2,3,5-position, 2,4,5-position, 2,4,6-position, 2,3,6-position or 3,4,5-position. If a phenyl residue carries substituents from the group consisting of methylenedioxy (—O—$CH_2$—O—) and ethylenedioxy (—O—$CH_2$—$CH_2$—O—), it preferably carries only one substituent from this group (if desired in addition to other substituents).

Substituted phenyl residues, which can represent $R^2$, include, for example, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 2,4,6-trimethylphenyl, 3,4,5-trimethylphenyl, 2-(n-butyl)phenyl, 3-(n-butyl)phenyl, 4-(n-butyl)phenyl, 2-isobutylphenyl, 3-isobutylphenyl, 4-isobutylphenyl, 3-tert-butylphenyl, 4-tert-butylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,4,5-trimethoxyphenyl, 2,4,6-trimethoxyphenyl, 3,4,5-trimethoxyphenyl, 2-(n-butoxy)phenyl, 3-(n-butoxy)phenyl, 4-(n-butoxy)phenyl, 2-isobutoxyphenyl, 3-isobutoxyphenyl, 4-isobutoxyphenyl, 2-tert-butoxyphenyl, 3-tert-butoxyphenyl, 4-tert-butoxyphenyl, 2,3-methylenedioxyphenyl, 3,4-methylenedioxyphenyl, 2,3-ethylenedioxyphenyl, 3,4-ethylenedioxyphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,4,5-trifluorophenyl, 2,4,6-trifluorophenyl, 3,4,5-trifluorophenyl, 2,3,5,6-tetrafluorophenyl, 2,3,4,5,6-pentafluorophenyl, 2-chloro-phenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2-bromophenyl, 3-bromophenyl, 4-bromophenyl, 3-iodophenyl, 4-iodophenyl, 2-trifluoromethylphenyl, 3-trifluoromethylphenyl, 4-trifluoromethylphenyl, 3,4-bis(trifluoromethyl)phenyl, 3,5-bis(trifluoromethyl)phenyl, 2-trifluoromethoxyphenyl, 3-trifluoromethoxyphenyl, or 4-trifluoromethoxyphenyl, etc. In substituted phenyl residues, also different substituents can be present in any desired combination, such as, for example, in the residues 3-methoxy-4-methylphenyl, 4-fluoro-3-methoxyphenyl, 3-fluoro-4-methoxyphenyl, 3,5-difluoro-4-methoxyphenyl, 3-fluoro-4,5-methylenedioxyphenyl, 3-fluoro-4,5-ethylenedioxyphenyl, 2-chloro-3-methylphenyl, 3-chloro-4-methylphenyl, or 3-chloro-4-fluorophenyl, etc.

Halogen is selected from the group consisting of fluorine, chlorine, bromine or iodine, preferably fluorine or chlorine. Pyridyl is selected from the group consisting of 2-pyridyl, 3-pyridyl and 4-pyridyl. The nitrogen atom also can be oxidized in pyridyl residues and the corresponding compound of formula I can be present as a pyridine N-oxide, which is also encompassed in the present invention.

Physiologically acceptable salts of the compounds of formula I are, in particular, non-toxic or pharmaceutically utilizable salts. Compounds of formula I, which contain acidic groups (e.g., a carboxylic acid group representing the group E), can be present as alkali metal salts or alkaline earth metal salts (e.g., sodium salts, potassium salts, magnesium salts and calcium salts), or as ammonium salts (e.g., salts with physiologically acceptable quaternary ammonium ions and acid addition salts with ammonia and physiologically acceptable organic amines, for example, methylamine, ethylamine, triethylamine, 2-hydroxy-ethylamine, tris(2-hydroxyethyl)amine, α,α,α-tris(hydroxymethyl)methylamine (tromethamine) or amino acids (e.g., basic amino acids)). Salts may comprise an acidic compound of formula I and an organic amine in a ratio of 1:1 or about 1:1 or in another ratio. For example, the acidic compound of formula I and the organic amine may be in a ratio of from about 1:0.5 to about 1:4 (i.e., 1 molecule of formula I per 0.5 to 4 molecules of the amine), and particularly in a ratio of from about 1:0.5 to about 1:2 (i.e., 1 molecule of formula I per 0.5 to 2 molecules of the amine).

Compounds of formula I, which contain basic groups (e.g., a pyridyl group), can be present as acid addition salts.

Examples of acid addition salts include salts with inorganic acids, for example, hydrochloric acid, sulfuric acid or phosphoric acid; or salts with organic carboxylic acids or sulfonic acids, such as acetic acid, citric acid, benzoic acid, maleic acid, fumaric acid, tartaric acid, methanesulfonic acid and p-toluenesulfonic acid. The present invention also encompasses compounds containing both acidic groups and basic groups, which can be present in the form of inner salts, zwitterions or betaines.

Salts can be obtained from the compounds of formula I by customary processes known to one of ordinary skill in the art, for example, by combining the compounds of formula I with an organic or inorganic acid or base in a solvent or diluent, or from other salts by anion exchange or cation exchange.

The compounds of formula I can be present in stereoisomeric forms. With respect to each asymmetric centers in the compounds of formula I, independently of any other asymmetric center, it is possible for the S configuration or the R configuration to be present or R/S mixtures to be present. Thus, the asymmetric carbon atom to which the residue $R^2$ is bonded can have the R configuration or S configuration or the compound of formula I can be present as an R/S mixture with respect to this carbon atom. Likewise, the asymmetric carbon atom to which the group A and the imidazolidine ring are bonded can have the R configuration or S configuration or the compound of formula I can be present as an R/S mixture with respect to this carbon atom. All other asymmetric carbon atoms can likewise have the R configuration or the S configuration, or the compound of formula I can be present as an R/S mixture with respect to each of these carbon atoms. In R/S mixtures the individual stereoisomers can be present in any ratio including a ratio of 1:1.

The invention includes all possible stereoisomers of the compounds of formula I, for example, pure or largely pure enantiomers, pure or largely pure diastereomers and mixtures of two or more stereoisomeric forms (e.g., mixtures of enantiomers and/or diastereomers) in all ratios. The invention thus relates to enantiomers in enantiomerically pure form, both as levorotatory and as dextrorotatory antipodes, in the form of racemates and in the form of mixtures of the two enantiomers in all ratios. The invention likewise relates to diastereomers in diastereomerically pure form and in the form of mixtures in all ratios. Examples of individual stereoisomers, which are comprised by the invention, are the compounds of formulae Ia, Ib, Ic and Id.

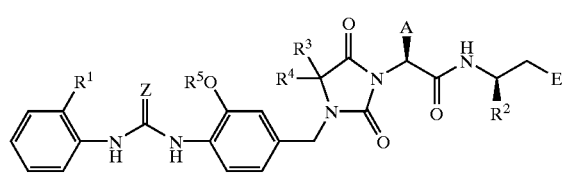

Ia

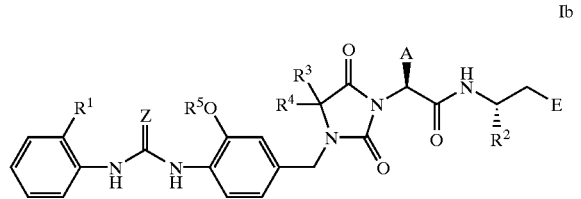

Ib

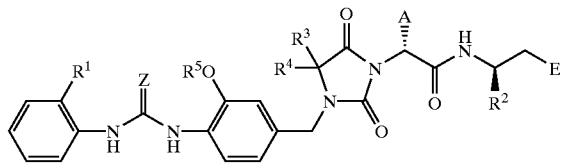

Ic

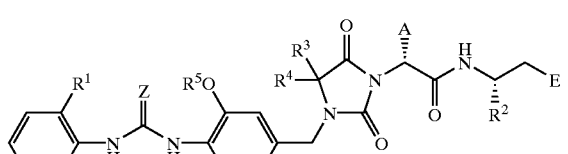

Id

The preparation of individual stereoisomers, if desired, can be carried out by use of stereochemically uniform starting substances in the synthesis, by stereoselective synthesis or by separation of a mixture according to customary methods (e.g., by chromatography or crystallization, and in the case of enantiomers, by chromatography on chiral phases). If appropriate, a derivatization can be carried out before a separation of stereoisomers. The separation of a stereoisomer mixture can be carried out at the stage of the compounds of formula I or at the stage of a starting substance or an intermediate in the course of the synthesis.

The compounds of formula I can contain mobile hydrogen atoms, i.e., they can be present in various tautomeric forms. The present invention comprises all tautomers of the compounds of formula I. The present invention also encompasses solvates and addition compounds or adducts of compounds of formula I, for example adducts with water, i.e., hydrates, or adducts with alcohols or amines. The invention further comprises derivatives of compounds of formula I (e.g., esters, amides, prodrugs, other physiologically acceptable derivatives), and active metabolites of compounds of formula I.

One embodiment encompasses prodrugs of the compounds of formula I, which in vitro are not necessarily pharmacologically active, but which in vivo and under physiological conditions are converted into active compounds of formula I. Suitable prodrugs of the compounds of formula I (i.e., chemically modified derivatives of the compounds of formula I having properties improved in a desired manner), are known to one of ordinary skill in the art. More detailed information regarding prodrugs is found, for example, in Fleisher et al., *Advanced Drug Delivery Reviews,* 19:115 (1996); Design of Prodrugs, H. Bundgaard, Ed., Elsevier, 1985; H. Bundgaard, Drugs of the Future 16:443(1991). Suitable prodrugs of the compounds of formula I are preferably ester prodrugs, amide prodrugs, aldehyde prodrugs and alcohol prodrugs of carboxylic acid groups (e.g., a carboxylic acid group representing the group E). The compounds of formula I, wherein the group E is hydroxymethyl, alkoxymethyl or formyl and which exhibit VLA-4 antagonism in vivo are prodrugs of the compounds of formula I wherein the group E is hydroxycarbonyl. Examples of ester prodrugs and amide prodrugs are $(C_1-C_4)$-alkyl esters (e.g., methyl esters, ethyl esters, isopropyl esters, or isobutyl esters), substituted alkyl esters (e.g., hydroxyalkyl esters, acyloxyalkyl esters, aminoalkyl esters, acylaminoalkyl esters, or dialkylaminoalkyl esters), unsubstituted amides or N—$(C_1-C_4)$-alkylamides (e.g., methylamides or ethylamides).

Examples of compounds of formula I are the following compounds of formulae Ie and If. The compounds of formulae Ie and If have the S configuration on the carbon atom which carries the group A; the S configuration on the carbon atom which carries the group $R^2$ if $R^2$ is phenyl or pyridyl; and have the R configuration on the carbon atom which carries the group $R^2$ if $R^2$ is methyl. The present invention also relates to the physiologically acceptable salts of the compounds of formulae Ie and If, for example, metal salts or salts with organic ammonium cations of compounds of formulae Ie and If which contain a carboxylic acid group, or acid additions salts of compounds of formulae Ie and If which contain pyridyl residues (e.g., hydrochlorides).

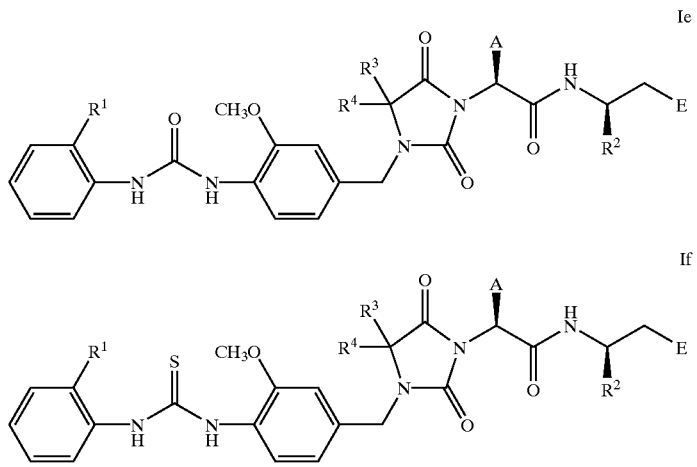

Compounds of formulae Ie and If:

| $R^1$ | $R^3$ | $R^4$ | A | $R^2$ | E |
|---|---|---|---|---|---|
| $CH_3$ | $CH_3$ | $CH_3$ | isobutyl | phenyl | COOH |
| $CH_3$ | $CH_3$ | $CH_3$ | isobutyl | phenyl | COONa |
| $CH_3$ | $CH_3$ | $CH_3$ | isobutyl | phenyl | $COOC_2H_5$ |
| $CH_3$ | $CH_3$ | $CH_3$ | isobutyl | phenyl | $COOiC_3H_7$ |
| $CH_3$ | $CH_3$ | $CH_3$ | isobutyl | phenyl | $CH_2OH$ |
| $CH_3$ | $CH_3$ | $CH_3$ | cyclopropylmethyl- | phenyl | COOH |
| $CH_3$ | $CH_3$ | $CH_3$ | cyclopropylmethyl- | phenyl | COONa |
| $CH_3$ | $CH_3$ | $CH_3$ | cyclopropylmethyl- | phenyl | $COOC_2H_5$ |
| $CH_3$ | $CH_3$ | $CH_3$ | cyclopropylmethyl- | phenyl | $COOiC_3H_7$ |
| $CH_3$ | $CH_3$ | $CH_3$ | cyclopropylmethyl- | phenyl | $CH_2OH$ |
| $CH_3$ | $CF_3$ | $CF_3$ | isobutyl | phenyl | COOH |
| $CH_3$ | $CF_3$ | $CF_3$ | isobutyl | phenyl | COONa |
| $CH_3$ | $CF_3$ | $CF_3$ | isobutyl | phenyl | $COOC_2H_5$ |
| $CH_3$ | $CF_3$ | $CF_3$ | isobutyl | phenyl | $COOiC_3H_7$ |
| $CH_3$ | $CF_3$ | $CF_3$ | isobutyl | phenyl | $CH_2OH$ |
| $CH_3$ | $CF_3$ | $CF_3$ | cyclopropylmethyl- | phenyl | COOH |
| $CH_3$ | $CF_3$ | $CF_3$ | cyclopropylmethyl- | phenyl | COONa |
| $CH_3$ | $CF_3$ | $CF_3$ | cyclopropylmethyl- | phenyl | $COOC_2H_5$ |
| $CH_3$ | $CF_3$ | $CF_3$ | cyclopropylmethyl- | phenyl | $COOiC_3H_7$ |
| $CH_3$ | $CF_3$ | $CF_3$ | cyclopropylmethyl- | phenyl | $CH_2OH$ |
| $CH_3$ | $CH_3$ | $CH_3$ | isobutyl | 2-pyridyl | COOH |
| $CH_3$ | $CH_3$ | $CH_3$ | isobutyl | 2-pyridyl | COONa |
| $CH_3$ | $CH_3$ | $CH_3$ | isobutyl | 2-pyridyl | $COOC_2H_5$ |
| $CH_3$ | $CH_3$ | $CH_3$ | isobutyl | 2-pyridyl | $COOiC_3H_7$ |
| $CH_3$ | $CH_3$ | $CH_3$ | cyclopropylmethyl- | 2-pyridyl | COOH |
| $CH_3$ | $CH_3$ | $CH_3$ | cyclopropylmethyl- | 2-pyridyl | COONa |
| $CH_3$ | $CH_3$ | $CH_3$ | cyclopropylmethyl- | 2-pyridyl | $COOC_2H_5$ |
| $CH_3$ | $CH_3$ | $CH_3$ | cyclopropylmethyl- | 2-pyridyl | $COOiC_3H_7$ |
| $CH_3$ | $CF_3$ | $CF_3$ | isobutyl | 2-pyridyl | COOH |
| $CH_3$ | $CF_3$ | $CF_3$ | isobutyl | 2-pyridyl | COONa |
| $CH_3$ | $CF_3$ | $CF_3$ | isobutyl | 2-pyridyl | $COOC_2H_5$ |
| $CH_3$ | $CF_3$ | $CF_3$ | isobutyl | 2-pyridyl | $COOiC_3H_7$ |
| $CH_3$ | $CF_3$ | $CF_3$ | cyclopropylmethyl- | 2-pyridyl | COOH |
| $CH_3$ | $CF_3$ | $CF_3$ | cyclopropylmethyl- | 2-pyridyl | COONa |
| $CH_3$ | $CF_3$ | $CF_3$ | cyclopropylmethyl- | 2-pyridyl | $COOC_2H_5$ |
| $CH_3$ | $CF_3$ | $CF_3$ | cyclopropylmethyl- | 2-pyridyl | $COOiC_3H_7$ |
| $CH_3$ | $CH_3$ | $CH_3$ | isobutyl | 3-pyridyl | COOH |
| $CH_3$ | $CH_3$ | $CH_3$ | isobutyl | 3-pyridyl | COONa |
| $CH_3$ | $CH_3$ | $CH_3$ | isobutyl | 3-pyridyl | $COOC_2H_5$ |
| $CH_3$ | $CH_3$ | $CH_3$ | isobutyl | 3-pyridyl | $COOiC_3H_7$ |
| $CH_3$ | $CH_3$ | $CH_3$ | cyclopropylmethyl- | 3-pyridyl | COOH |
| $CH_3$ | $CH_3$ | $CH_3$ | cyclopropylmethyl- | 3-pyridyl | COONa |

-continued

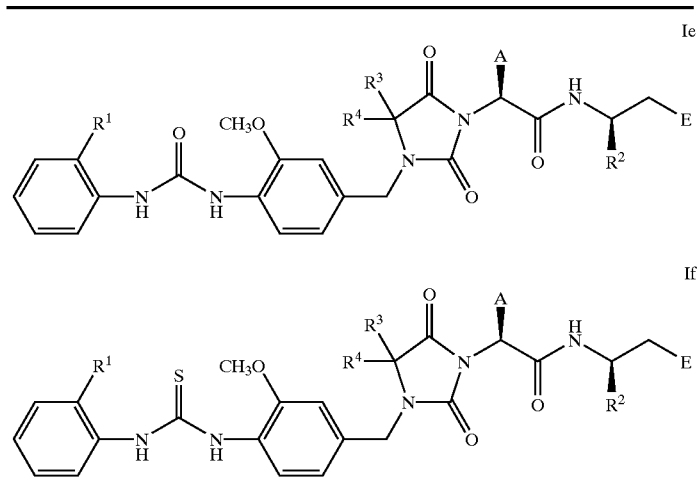

Compounds of formulae Ie and If:

| R¹ | R³ | R⁴ | A | R² | E |
|---|---|---|---|---|---|
| CH₃ | CH₃ | CH₃ | cyclopropylmethyl- | 3-pyridyl | COOC₂H₅ |
| CH₃ | CH₃ | CH₃ | cyclopropylmethyl- | 3-pyridyl | COOiC₃H₇ |
| CH₃ | CF₃ | CF₃ | isobutyl | 3-pyridyl | COOH |
| CH₃ | CF₃ | CF₃ | isobutyl | 3-pyridyl | COONa |
| CH₃ | CF₃ | CF₃ | isobutyl | 3-pyridyl | COOC₂H₅ |
| CH₃ | CF₃ | CF₃ | isobutyl | 3-pyridyl | COOiC₃H₇ |
| CH₃ | CF₃ | CF₃ | cyclopropylmethyl- | 3-pyridyl | COOH |
| CH₃ | CF₃ | CF₃ | cyclopropylmethyl- | 3-pyridyl | COONa |
| CH₃ | CF₃ | CF₃ | cyclopropylmethyl- | 3-pyridyl | COOC₂H₅ |
| CH₃ | CF₃ | CF₃ | cyclopropylmethyl- | 3-pyridyl | COOiC₃H₇ |
| CH₃ | CH₃ | CH₃ | isobutyl | 4-pyridyl | COOH |
| CH₃ | CH₃ | CH₃ | isobutyl | 4-pyridyl | COONa |
| CH₃ | CH₃ | CH₃ | isobutyl | 4-pyridyl | COOC₂H₅ |
| CH₃ | CH₃ | CH₃ | isobutyl | 4-pyridyl | COOiC₃H₇ |
| CH₃ | CH₃ | CH₃ | cyclopropylmethyl- | 4-pyridyl | COOH |
| CH₃ | CH₃ | CH₃ | cyclopropylmethyl- | 4-pyridyl | COONa |
| CH₃ | CH₃ | CH₃ | cyclopropylmethyl- | 4-pyridyl | COOC₂H₅ |
| CH₃ | CH₃ | CH₃ | cyclopropylmethyl- | 4-pyridyl | COOiC₃H₇ |
| CH₃ | CF₃ | CF₃ | isobutyl | 4-pyridyl | COOH |
| CH₃ | CF₃ | CF₃ | isobutyl | 4-pyridyl | COONa |
| CH₃ | CF₃ | CF₃ | isobutyl | 4-pyridyl | COOC₂H₅ |
| CH₃ | CF₃ | CF₃ | isobutyl | 4-pyridyl | COOiC₃H₇ |
| CH₃ | CF₃ | CF₃ | cyclopropylmethyl- | 4-pyridyl | COOH |
| CH₃ | CF₃ | CF₃ | cyclopropylmethyl- | 4-pyridyl | COONa |
| CH₃ | CF₃ | CF₃ | cyclopropylmethyl- | 4-pyridyl | COOC₂H₅ |
| CH₃ | CF₃ | CF₃ | cyclopropylmethyl- | 4-pyridyl | COOiC₃H₇ |
| CH₃ | CH₃ | CH₃ | isobutyl | methyl | COOH |
| CH₃ | CH₃ | CH₃ | isobutyl | methyl | COONa |
| CH₃ | CH₃ | CH₃ | isobutyl | methyl | COOC₂H₅ |
| CH₃ | CH₃ | CH₃ | isobutyl | methyl | COOiC₃H₇ |
| CH₃ | CH₃ | CH₃ | isobutyl | methyl | CH₂OH |
| CH₃ | CH₃ | CH₃ | cyclopropylmethyl- | methyl | COOH |
| CH₃ | CH₃ | CH₃ | cyclopropylmethyl- | methyl | COONa |
| CH₃ | CH₃ | CH₃ | cyclopropylmethyl- | methyl | COOC₂H₅ |
| CH₃ | CH₃ | CH₃ | cyclopropylmethyl- | methyl | COOiC₃H₇ |
| CH₃ | CH₃ | CH₃ | cyclopropylmethyl- | methyl | CH₂OH |
| CH₃ | CF₃ | CF₃ | isobutyl | methyl | COOH |
| CH₃ | CF₃ | CF₃ | isobutyl | methyl | COONa |
| CH₃ | CF₃ | CF₃ | isobutyl | methyl | COOC₂H₅ |
| CH₃ | CF₃ | CF₃ | isobutyl | methyl | COOiC₃H₇ |
| CH₃ | CF₃ | CF₃ | isobutyl | methyl | CH₂OH |
| CH₃ | CF₃ | CF₃ | cyclopropylmethyl- | methyl | COOH |
| CH₃ | CF₃ | CF₃ | cyclopropylmethyl- | methyl | COONa |
| CH₃ | CF₃ | CF₃ | cyclopropylmethyl- | methyl | COOC₂H₅ |
| CH₃ | CF₃ | CF₃ | cyclopropylmethyl- | methyl | COOiC₃H₇ |
| CH₃ | CF₃ | CF₃ | cyclopropylmethyl- | methyl | CH₂OH |
| H | CH₃ | CH₃ | isobutyl | phenyl | COOH |
| H | CH₃ | CH₃ | isobutyl | phenyl | COONa |
| H | CH₃ | CH₃ | isobutyl | phenyl | COOC₂H₅ |
| H | CH₃ | CH₃ | isobutyl | phenyl | COOiC₃H₇ |
| H | CH₃ | CH₃ | isobutyl | phenyl | CH₂OH |
| H | CH₃ | CH₃ | cyclopropylmethyl- | phenyl | COOH |

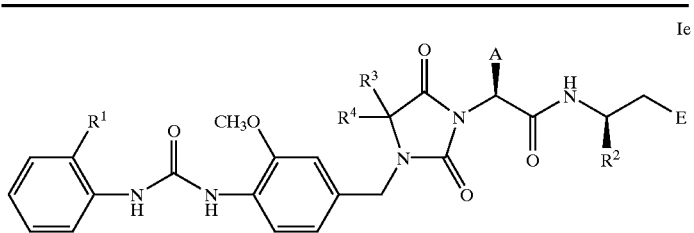

Ie

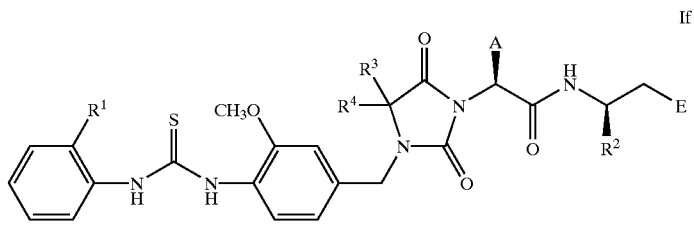

If

Compounds of formulae Ie and If:

| R¹ | R³ | R⁴ | A | R² | E |
|---|---|---|---|---|---|
| H | CH₃ | CH₃ | cyclopropylmethyl- | phenyl | COONa |
| H | CH₃ | CH₃ | cyclopropylmethyl- | phenyl | COOC₂H₅ |
| H | CH₃ | CH₃ | cyclopropylmethyl- | phenyl | COOiC₃H₇ |
| H | CH₃ | CH₃ | cyclopropylmethyl- | phenyl | CH₂OH |
| H | CF₃ | CF₃ | isobutyl | phenyl | COOH |
| H | CF₃ | CF₃ | isobutyl | phenyl | COONa |
| H | CF₃ | CF₃ | isobutyl | phenyl | COOC₂H₅ |
| H | CF₃ | CF₃ | isobutyl | phenyl | COOiC₃H₇ |
| H | CF₃ | CF₃ | isobutyl | phenyl | CH₂OH |
| H | CF₃ | CF₃ | cyclopropylmethyl- | phenyl | COOH |
| H | CF₃ | CF₃ | cyclopropylmethyl- | phenyl | COONa |
| H | CF₃ | CF₃ | cyclopropylmethyl- | phenyl | COOC₂H₅ |
| H | CF₃ | CF₃ | cyclopropylmethyl- | phenyl | COOiC₃H₇ |
| H | CF₃ | CF₃ | cyclopropylmethyl- | phenyl | CH₂OH |
| H | CH₃ | CH₃ | isobutyl | methyl | COOH |
| H | CH₃ | CH₃ | isobutyl | methyl | COONa |
| H | CH₃ | CH₃ | isobutyl | methyl | COOC₂H₅ |
| H | CH₃ | CH₃ | isobutyl | methyl | COOiC₃H₇ |
| H | CH₃ | CH₃ | isobutyl | methyl | CH₂OH |
| H | CH₃ | CH₃ | cyclopropylmethyl- | methyl | COOH |
| H | CH₃ | CH₃ | cyclopropylmethyl- | methyl | COONa |
| H | CH₃ | CH₃ | cyclopropylmethyl- | methyl | COOC₂H₅ |
| H | CH₃ | CH₃ | cyclopropylmethyl- | methyl | COOiC₃H₇ |
| H | CH₃ | CH₃ | cyclopropylmethyl- | methyl | CH₂OH |
| H | CF₃ | CF₃ | isobutyl | methyl | COOH |
| H | CF₃ | CF₃ | isobutyl | methyl | COONa |
| H | CF₃ | CF₃ | isobutyl | methyl | COOC₂H₅ |
| H | CF₃ | CF₃ | isobutyl | methyl | COOiC₃H₇ |
| H | CF₃ | CF₃ | isobutyl | methyl | CH₂OH |
| H | CF₃ | CF₃ | cyclopropylmethyl- | methyl | COOH |
| H | CF₃ | CF₃ | cyclopropylmethyl- | methyl | COONa |
| H | CF₃ | CF₃ | cyclopropylmethyl- | methyl | COOC₂H₅ |
| H | CF₃ | CF₃ | cyclopropylmethyl- | methyl | COOiC₃H₇ |
| H | CF₃ | CF₃ | cyclopropylmethyl- | methyl | CH₂OH |

The individual structural elements in the compounds of formula I preferably have the following meanings, which they can have independently of one another.

$R^2$ is preferably $(C_1-C_4)$-alkyl, which can be substituted by one or more fluorine atoms; or pyridyl; or unsubstituted phenyl; or phenyl, which is substituted by a methylenedioxy residue or an ethylenedioxy residue; or phenyl, which is substituted by one or two $(C_1-C_4)$-alkoxy groups. The alkyl group representing $R^2$, which can optionally be substituted by fluorine, is preferably selected from the group consisting of methyl, ethyl, isopropyl, trifluoromethyl and 2,2,2-trifluoroethyl. The alkoxy substituents in a phenyl group representing $R^2$ are preferably methoxy groups. More preferably, $R^2$ is selected from the group consisting of methyl, pyridyl, unsubstituted phenyl, phenyl substituted by a methylenedioxy residue or an ethylenedioxy residue, and phenyl substituted by one or two methoxy groups. Most preferably, $R^2$ is selected from the group consisting of methyl, unsubstituted phenyl and pyridyl.

$R^3$ and $R^4$ can be identical or different. Preferably, $R^3$ and $R^4$ are identical. In one embodiment, $R^3$ and $R^4$ are both methyl. In another embodiment, $R^3$ and $R^4$ are both trifluoromethyl.

An alkyl group representing $R^5$, which can be substituted by one or more fluorine atoms, is preferably a methyl group, ethyl group or trifluoromethyl group. Preferably, $R^5$ is $(C_1-C_4)$-alkyl, which can be substituted by one or more fluorine atoms. More preferably, $R^5$ is methyl or trifluoromethyl, and most preferably, methyl.

$R^6$ is preferably hydroxyl, $(C_1-C_6)$-alkoxy, phenyl-$(C_1-C_4)$-alkoxy, phenyloxy or amino ($NH_2$) and more preferably hydroxyl, $(C_1-C_6)$-alkoxy or amino. R is even more preferably hydroxyl or $(C_1-C_6)$-alkoxy, and most preferably hydroxyl or $(C_1-C_4)$-alkoxy, in particular hydroxyl.

$R^7$ is preferably hydrogen or $(C_1-C_3)$-alkyl, more preferably hydrogen or methyl, and most preferably hydrogen.

E is preferably —CO—$R^6$, —CO—H, —$CH_2$—OH or —$CH_2$—$OCH_3$, more preferably —CO—$R^6$, —$CH_2$—OH or —$CH_2$—$OCH_3$, even more preferably —CO—$R^6$ or —$CH_2$—OH, and most preferably —COOH, —$COOC_2H_5$, —$COOiC_3H_7$ or —$CH_2$—OH, in particular —COOH.

In other embodiments of the invention, Z is sulfur or oxygen.

In other embodiments of the present invention, A is the isobutyl residue (2-methylpropyl residue, i.e., $(CH_3)_2CH$—$CH_2$—) or cyclopropylmethyl residue (i.e., cyclopropyl-$CH_2$—). In other embodiments of the present invention, $R^1$ is hydrogen or methyl.

The present invention encompasses compounds of formula I having a uniform configuration on one or more chiral centers, including, for example, on the carbon atom carrying the residue $R^2$, and/or on the carbon atom carrying the residue A and the imidazolidine residue. Preferred compounds of formula I have a uniform or essentially uniform configuration on one or more chiral centers, either the R configuration or the S configuration, but are not present as an R/S mixture. However, the individual chiral centers in these compounds of formula I can, independently of one another, have the R or S configuration and have identical or different configurations. More preferred compounds of formula I are those wherein the carbon atom carrying the residue A and the imidazolidine residue is present in the S configuration, i.e., in the configuration with respect to this stereocenter which is shown in formulae Ia and Ib. More preferred compounds of formula I also include those wherein the carbon atom carrying the group $R^2$ is present in the configuration shown in formulae Ia and Ic. If $R^2$, for example, is phenyl, substituted phenyl or pyridyl in these more preferred compounds, the carbon atom carrying the group $R^2$ has the S configuration. Alternatively, if $R^2$ is methyl, ethyl or isobutyl in these more preferred compounds the carbon atom carrying the group $R^2$ has the R configuration. Most preferred compounds of formula I are those in which the two above-mentioned stereocenters are present in the configurations shown in formula Ia.

Preferred compounds of formula I include compounds having all combinations of residues as described herein. Examples of preferred compounds are, for example, compounds in which, simultaneously, $R^1$, $R^3$, $R^4$ and $R^5$ are methyl and A is isobutyl; compounds in which, simultaneously, $R^1$, $R^3$, $R^4$ and $R^5$ are methyl and A is cyclopropylmethyl; compounds in which, simultaneously, $R^1$ is methyl, $R^3$ and $R^4$ are trifluoromethyl, $R^5$ is methyl and A is isobutyl; compounds in which, simultaneously, $R^1$ is methyl, $R^3$ and $R^4$ are trifluoromethyl, $R^5$ is methyl and A is cyclopropylmethyl; compounds in which, simultaneously, $R^1$ is hydrogen, $R^3$, $R^4$ and $R^5$ are methyl and A is isobutyl; compounds in which, simultaneously, $R^1$ is hydrogen, $R^3$, $R^4$ and $R^5$ are methyl and A is cyclopropylmethyl; compounds in which, simultaneously, $R^1$ is hydrogen, $R^3$ and $R^4$ are trifluoromethyl, $R^5$ is methyl and A is isobutyl; or compounds in which, simultaneously, $R^1$ is hydrogen, $R^3$ and $R^4$ are trifluoromethyl, $R^5$ is methyl and A is cyclopropylmethyl, and the other groups have the general or preferred, or specific meanings defined herein.

Another preferred embodiment of the invention comprises, for example, compounds of formula I, wherein
A is cyclopropylmethyl- or isobutyl;
E is —CO—$R^6$ or —$CH_2$—OH;
Z is oxygen;
$R^1$ is hydrogen or methyl;
$R^2$ is pyridyl, unsubstituted phenyl, phenyl substituted by a methylenedioxy residue or an ethylenedioxy residue, phenyl substituted by one or two $(C_1-C_4)$-alkoxy groups, or $(C_1-C_4)$-alkyl which can be substituted by one or more fluorine atoms;
$R^3$ and $R^4$ are methyl;
$R^5$ is methyl;
$R^6$ is hydroxyl, $(C_1-C_6)$-alkoxy, phenyl-$(C_1-C_4)$-alkoxy, phenyloxy or amino;
in all their stereoisomeric forms and mixtures thereof in all ratios,
and their physiologically acceptable salts.

Another preferred embodiment of the invention comprises, for example, compounds of formula I, wherein
A is cyclopropylmethyl- or isobutyl;
E is —COOH, —$COOC_2H_5$, —$COOiC_3H_7$ or —$CH_2$—OH;
Z is oxygen;
$R^1$ is methyl;
$R^2$ is pyridyl, unsubstituted phenyl, phenyl substituted by a methylenedioxy residue or an ethylenedioxy residue, phenyl substituted by one or two methoxy groups, or $(C_1-C_4)$-alkyl which can be substituted by one or more fluorine atoms;
$R^3$ and $R^4$ are methyl;
$R^5$ is methyl;
in all their stereoisomeric forms and mixtures thereof in all ratios,
and their physiologically acceptable salts.

Another more preferred embodiment of the invention comprises, for example, compounds of formula I, wherein
A is cyclopropylmethyl- or isobutyl;
E is —COOH, —$COOC_2H_5$, —$COOiC_3H_7$ or —$CH_2$—OH;
Z is oxygen;
$R^1$ is methyl;
$R^2$ is unsubstituted phenyl, pyridyl, methyl or 2,2,2-trifluoroethyl;
$R^3$ and $R^4$ are methyl;
$R^5$ is methyl;
in all their stereoisomeric forms and mixtures thereof in all ratios,
and their physiologically acceptable salts.

Another more preferred embodiment of the invention comprises, for example, compounds of formula I, wherein
A is cyclopropylmethyl- or isobutyl;
E is —COOH, —$COOC_2H_5$, —$COOiC_3H_7$ or —$CH_2$—OH;
Z is oxygen;
$R^1$ is methyl;
$R^2$ is unsubstituted phenyl, pyridyl or methyl;
$R^3$ and $R^4$ are methyl; $R^5$ is methyl;
in all their stereoisomeric forms and mixtures thereof in all ratios,
and their physiologically acceptable salts.

All above definitions of subgroups of the compounds of formula I apply analogously for compounds of formula I, wherein $R^3$ and $R^4$ are both trifluoromethyl instead of methyl. Thus, for example, more preferred compounds are also compounds of formula I, wherein
A is cyclopropylmethyl- or isobutyl;
E is —COOH, —$COOC_2H_5$, —$COOiC_3H_7$ or —$CH_2$—OH;
Z is oxygen;

$R^1$ is methyl;
$R^2$ is unsubstituted phenyl, pyridyl or methyl;
$R^3$ and $R^4$ are trifluoromethyl; $R^5$ is methyl;
in all their stereoisomeric forms and mixtures thereof in all ratios,
and their physiologically acceptable salts.

The compounds of formula I can be prepared, for example, by condensation of a compound of formula II

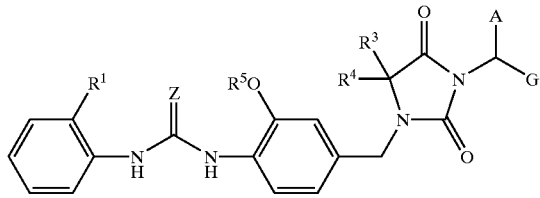

with a compound of formula III,

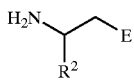

where in formulae II and III the groups A, E, Z, $R^1$, $R^2$, $R^3$, $R^4$ and $R^5$ are as defined hereinabove, or alternatively, functional groups can be present in these groups in protected form or in the form of precursors, and where G is hydroxycarbonyl, $(C_1-C_6)$-alkoxycarbonyl or activated carboxylic acid derivatives such as, for example, acid chlorides or active esters.

In the condensation of the compounds of formulae II and III, it is generally necessary that a carboxylic acid group, which is present but not involved in the condensation reaction, is protected by a reversible protective group and then is present, for example, in the form of a suitable $(C_1-C_6)$-alkyl ester (e.g., tert-butyl ester) or the benzyl ester. In the preparation of compounds of formula I, wherein the group E is a hydroxycarbonyl group or a derivative of a hydroxycarbonyl group, the residue E in the compounds of formula III can first be a hydroxycarbonyl group present in protected form and then, after the condensation of the compounds of formulae II and III, the hydroxycarbonyl group can be liberated and/or the desired final group E can be synthesized in one or more further steps.

Functional group precursors are groups that can be converted into a desired functional group using typical synthetic processes known to one of ordinary skill in the art. For example, a cyano group, which can be converted into a carboxylic acid group by hydrolysis, can be designated as a precursor for the carboxylic acid group. An alcohol group, which can be oxidized to an aldehyde group, can be designated as a precursor for the aldehyde group. Examples of protective groups, which may be introduced before carrying out a reaction or a reaction sequence and are later removed again, have already been described herein.

The coupling methods of peptide chemistry, which are well known to one of ordinary skill in the art, are advantageously used in the condensation of the compounds of formulae II and III (see, for example, Houben-Weyl, Methoden der Organischen Chemie [Methods of Organic Chemistry], Volume 15/1 and 15/2, Georg Thieme Verlag, Stuttgart, 1974). Possible condensing agents or coupling reagents are, for example, carbonyldiimidazole, carbodiimides (e.g., dicyclohexylcarbodiimide (DCC) or diisopropylcarbodiimide), O-((cyano(ethoxycarbonyl)methylene)amino)—N,N,N',N'-tetramethyluronium tetrafluoroborate (TOTU) or propylphosphonic anhydride (PPA). The condensations can be carried out under standard conditions well known to one of ordinary skill in the art. In general, the condensations are carried out in an inert solvent or diluent, (e.g., an aprotic solvent, such as N,N-dimethylformamide (DMF), dimethyl sulfoxide (DMSO), N-methyl-2-pyrrolidone (NMP), tetrahydrofuran (THF) or dimethoxyethane (DME)). Depending on the condensation carried out in the individual case, it may be advantageous to add a base, such as a tertiary amine or auxiliary reagents, such as an N-hydroxy compound (e.g., 1-hydroxybenzotriazole (HOBT)). The work-up of the reaction mixture and a purification of the product can be carried out according to customary standard processes known to one of ordinary skill in the art. After condensation, any protective groups present are removed by methods known to one of ordinary skill in the art, including hydrogenation, hydrolysis and acid work-up. For example, benzyl groups in benzyl esters can be removed by catalytic hydrogenation, or protective groups of the tert-butyl type can be removed by treatment with a suitable acid. The preparation of the compounds of formula I also can be carried out, for example, by synthesizing the compounds stepwise on a solid phase using customary methods known to one of ordinary skill in the art, and it is possible to introduce individual structural elements of the molecule in different sequences.

The amino compounds of formula III are commercially available or can be synthesized, according to or analogously to well-known standard processes, from commercially available starting compounds or starting compounds that are obtainable according to or analogously to literature procedures. For example, optically active 3-substituted 3-aminopropionic acids of formula III or their esters(e.g., 3-phenyl-3-aminopropionic acid esters) can be prepared from the corresponding 3-substituted acrylic acids that are obtainable from their corresponding aldehydes. The 3-substituted acrylic acids are converted, by reaction with oxalyl chloride, into the acid chlorides, which further are converted, by reaction with an alcohol, into the esters(e.g., using tert-butanol to convert acid chlorides into the tert-butyl esters). To form the amino compound, the esters are then reacted with the lithium salt of an optically active amine (e.g., the lithium salt of (R)-(+)-N-benzyl-N-(1-phenylethyl)amine), and then the benzyl group and the phenylethyl group in the 3-substituted tert-butyl 3-(N-benzyl-N-(1-phenylethyl)amino)propionate obtained are removed by catalytic hydrogenation. For the preparation of compounds of formula III, wherein E is the hydroxymethyl group $CH_2OH$ or an etherified hydroxymethyl group, it is possible to employ 3-substituted 3-aminopropanols or their ethers in the condensation reaction. The 3-substituted 3-aminopropanols or their ethers are obtainable from the 3-substituted 3-aminopropionic acids or their esters by reduction of the acid group or the ester group (e.g., from the ethyl ester or tert-butyl ester) using lithium aluminum hydride or lithium aluminum hydride/aluminum trichloride.

Compounds of formula II can be prepared, for example, by first reacting compounds of formula IV

IV in a Bucherer reaction (e.g., with ammonium carbonate and potassium cyanide) to give compounds of formula V

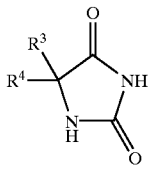

V which further are reacted with an alkylating reagent of the formula LG—CHA—G, which introduces the residue of the formula —CHA—G into the molecule, to give compounds of formula VI,

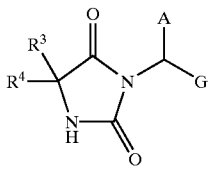

VI where A, $R^3$, $R^4$ and G are defined as indicated above. The reaction of compounds of formula VI with a second alkylating reagent of formula VII,

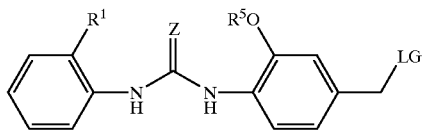

VII wherein Z, $R^1$ and $R^5$ are defined as indicated above, gives the corresponding compounds of formula II. The group LG is a nucleophilically substitutable leaving group, for example halogen (e.g., chlorine or bromine), or sulfonyloxy (e.g., tosyloxy, methylsulfonyloxy or trifluoromethylsulfonyloxy).

Compounds of formula II also can be prepared, for example, by initially reacting a compound of formula VI with a reagent of the formula 4—(PG—NH)—$C_6H_3$(OR$^5$)—$CH_2$—LG, wherein LG is a nucleophilically substitutable leaving group as described herein, to give a compound of formula VIII,

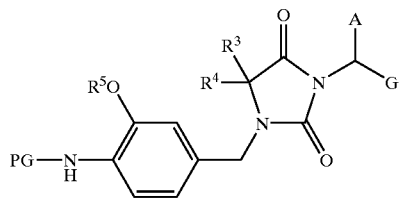

VIII where the meanings indicated above apply for A, G, $R^3$, $R^4$ and $R^5$ and PG is an amino protective group(e.g., tert-butoxycarbonyl or benzyloxycarbonyl). After removal of the protective group PG, the compounds of formula II are obtained by reaction of the resulting amino group $H_2N$ with phenyl isocyanate, phenyl isothiocyanate, 2-methylphenyl isocyanate or 2-methylphenyl isothiocyanate. Similar to the compounds of formula VIII, compounds can be prepared and employed in the synthesis, wherein the group PG—NH— in formula VIII is replaced by a precursor for an amino group, which is then converted into an amino group in a further reaction step. For example, a compound of formula VI can initially be reacted with a nitro compound of the formula 4—$O_2N$—$C_6H_3$(OR$^5$)—$CH_2$—LG to give a compound corresponding formula VIII and the nitro group can further be converted into the amino group (e.g. by catalytic hydrogenation). Thereafter, the amino group can be converted into the desired compound of formula II by reaction with phenyl isocyanate, phenyl isothiocyanate, 2-methylphenyl isocyanate or 2-methylphenyl isothiocyanate.

In general, each step in the preparation of the compounds of formula I can be carried out according to or analogously to known methods familiar to one of ordinary skill in the art. Depending on each particular synthesis, it may be appropriate to temporarily block functional groups, which could lead to side reactions or undesired reactions, by means of a protective group strategy suited to the specific synthesis problem. Such a procedure, which is known to one of ordinary skill in the art, may be applied in any step of the synthesis of the compounds of formula I.

Compounds of formula I also can be obtained by reacting N-substituted amino acids or preferably of their esters, such as methyl esters, ethyl esters, tert-butyl esters or benzyl esters, for example the amino acid methyl esters of formula IX,

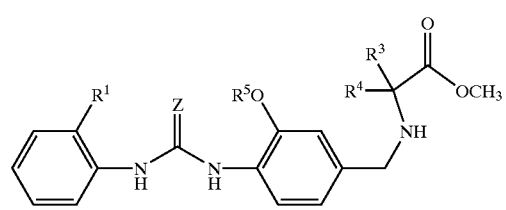

IX wherein Z, $R^1$, $R^3$, $R^4$ and $R^5$ are defined as indicated above, with isocyanates of formula X,

X

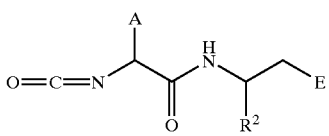

wherein A, E and R² are defined as indicated above. The amino acid methyl esters of formula IX and other esters and the respective amino acids are obtainable according to standard processes. The isocyanates of formula X are obtainable according to standard processes from the corresponding compounds which instead of the isocyanate group contain an H₂N group. The reaction of the compounds of formulae IX and X provides urea derivatives of formula XI,

XI

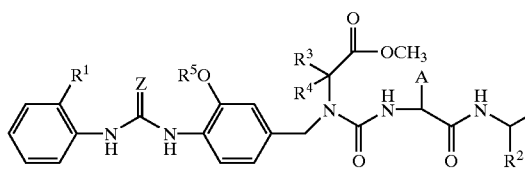

wherein R¹, R², R³, R⁴, R⁵, Z, E and A are defined as indicated above. The compounds of formula XI then can be cyclized by heating with acids to give compounds of formula I. The cyclization of the compounds of formula XI to compounds of formula I also can be carried out by treatment with bases in inert solvents (e.g. by treatment with sodium hydride in an aprotic solvent, such as dimethylformamide). During the reactions, as explained above, functional groups can be present in protected form.

Compounds of formula I also can be obtained by reacting a compound of formula IX with an isocyanate of formula XII

XII

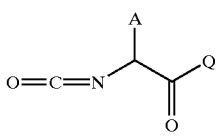

wherein A has the meanings indicated above and Q, for example, is an alkoxy group (e.g., a (C₁–C₄)-alkoxy group, such as methoxy, ethoxy or tert-butoxy), or a (C₆–C₁₄)-aryl-(C₁–C₄)-alkoxy group (e.g., benzyloxy). In this reaction, a compound of formula XIII is obtained,

XIII

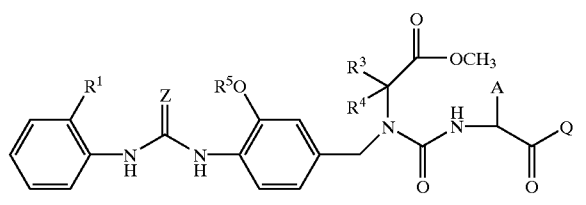

wherein A, Q, Z, R¹, R³, R⁴ and R⁵ are defined as indicated above The compound of formula XIII then is cyclized by reaction with an acid or a base, as described above for the cyclization of the compounds of formula XI, to a compound of formula XIV,

XIV

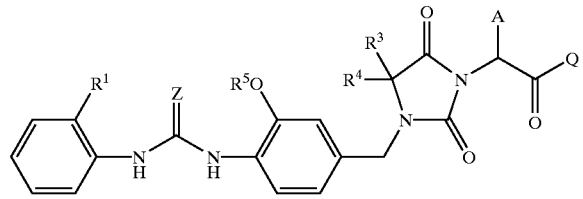

wherein A, Q, Z, R¹, R³, R⁴ and R⁵ are defined as indicated above. The group CO—Q in the compound of formula XIV may be converted into the carboxylic acid group COOH, for example, by hydrolysis. The conversion of the group CO—Q into the group COOH also can be carried out simultaneously with the cyclization if the cyclization of the compound of formula XIII to the compound of formula XIV is carried out using an acid. A compound of formula I is obtained by subsequent coupling with a compound of formula III, as described above for the coupling of the compounds of formulae II and III. Functional groups can be present in protected form or in the form of precursors in this synthetic process.

A further method for preparing compounds of formula I is, for example, the reaction of compounds of formula XV,

XV

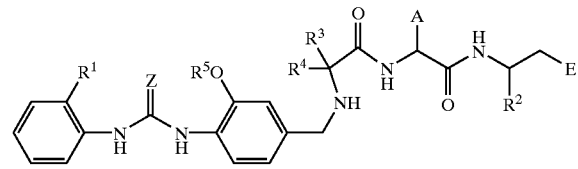

for which the definitions indicated above apply, with phosgene or other chemical equivalents thereof (analogously to S. Goldschmidt and M. Wick, *Liebigs Ann. Chem.*, 575:217 (1952) and C. Tropp, *Chem. Ber.*, 61:1431 (1928)).

Compounds of formula I also can be prepared by coupling a compound of formula XVI,

XVI

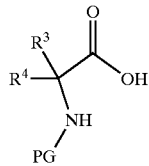

with a compound of formula XVII,

XVII

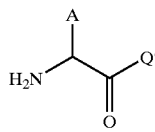

to give a compound of formula XVIII

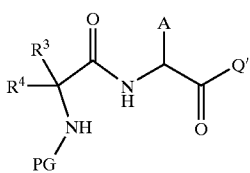

XVIII wherein A, R³ and R⁴ have the meanings indicated above, PG is an amino protective group (e.g., a benzyloxycarbonyl group) and Q' is a protected carboxylic acid hydroxyl group(e.g., an alkoxy group, such as tert-butoxy) in formulae XVI, XVII and XVIII. The protective group PG in the compound of formula XVIII then can be removed selectively from the amino group, for example, by hydrogenation in the case of a benzyloxycarbonyl group, and by introduction of a CO group to facilitate a ring closure, giving a compound of formula XIX is obtained

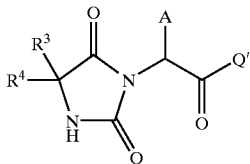

XIX wherein A, R³, R⁴ and Q' have the meanings indicated above. It is possible to use, for example, phosgene or a phosgene equivalent, such as diphosgene (analogously to the reaction of the compounds of formula XV explained above), in the step of introducing the carbonyl group. As an intermediate, it is possible, for example, for an isocyanate to occur or to be prepared specifically, in the conversion of the compound of formula XVIII into the compound of formula XIX. The conversion of the compound of formula XVIII into the compound of formula XIX can be carried out in one or more steps. For example, the carbonyl group initially can be introduced and then the cyclization can be carried out, in a separate step, in the presence of a base such as sodium hydride as described for the cyclizations mentioned above. Compounds of formula XVIII, wherein PG is the benzyloxycarbonyl group also can be converted directly into compounds of formula XIX, without a synthetic building block, such as phosgene being employed for the introduction of the carbonyl group. If compounds of formula XVIII, wherein PG is benzyloxycarbonyl, are treated with a base (e.g., sodium hydride), the compounds of formula XIX can be obtained directly. The compounds of formula XIX then can be alkylated, as explained above for the compounds of formula VI, on the NH group using a reagent of formula VII and the desired compounds of formula I can be synthesized, as described above for the compounds of formulae VI and II, after conversion of the protected carboxylic acid group CO—Q' into the carboxylic acid group COOH. Functional groups can be present in protected form or in the form of precursors in this synthetic process.

In addition, compounds of formula I can be prepared by firstly reacting a compound of formula XX

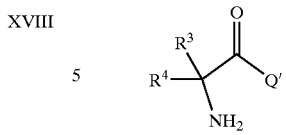

XX with an isocyanate of formula XII to give a compound of formula XXI,

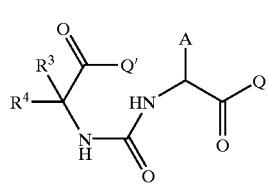

XXI wherein A, R³, R⁴, Q and Q' in formulae XX and XXI have the meanings indicated above. The compound of formula XXI then is cyclized by treating with a strong acid (e.g., semiconcentrated hydrochloric acid) to give a compound of formula XXII.

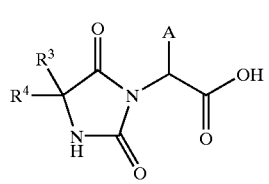

XXII

Compounds of formula XXII also can be prepared starting from a compound of formula XVIII, wherein A, R³, R⁴ and Q' have the meanings indicated; and PG is an alkoxycarbonyl group (e.g., ($C_1$–$C_4$)-alkoxycarbonyl), an ($C_6$–$C_{14}$)-aryl-($C_1$–$C_4$)-alkoxycarbonyl group (e.g., phenyl-($C_1$–$C_4$)-alkoxycarbonyl), or an ($C_6$–$C_{14}$)-aryloxycarbonyl group (e.g., phenyloxycarbonyl). This starting compound of formula XVIII is converted, by liberating the protected carboxylic acid group CO—Q', into a compound of formula XVIII, wherein CO—Q' is the free carboxylic acid group CO—OH; PG is ($C_1$–$C_4$)-alkoxycarbonyl, ($C_6$–$C_{14}$)-aryl-($C_1$–$C_4$)-alkoxycarbonyl or ($C_6$–$C_{14}$)-aryloxycarbonyl; and A, R³ and R⁴ have the meanings indicated above. The obtained compound of formula XVIII is cyclized to the compound of formula XXII by reaction with a base (e.g., sodium carbonate).

Compounds of formula IIa,

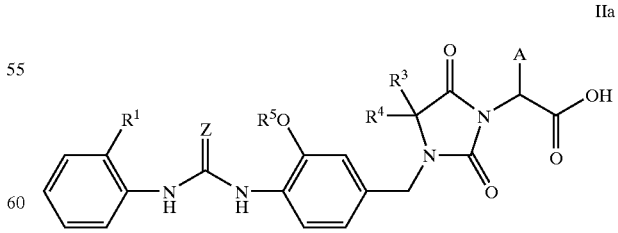

IIa wherein A, Z, R¹, R³, R⁴ and R⁵ have the meanings indicated above, then can be obtained by reacting the compounds of formula XXII with an alkylating reagent of formula VII in the presence of excess base (e.g., in the presence of an excess of n-butyllithium), and then acidifying. The 4-(3- arylureido)benzyl group or 4-(3-arylthioureido)benzyl group also can be introduced stepwise into the compounds of formula XXII, which is analogous to the preparation of the compounds of formula VIII and the compounds of formula II obtained therefrom.

Compounds of formula I, wherein the residues $R^3$ and $R^4$ are trifluoromethyl, advantageously can be prepared by reacting an isonitrile of formula XXIII with 2-tert-butoxy-4,4-bis(trifluoromethyl)-1,3-oxazabuta-1,3-diene of formula XXIV to give a compound of formula XXV,

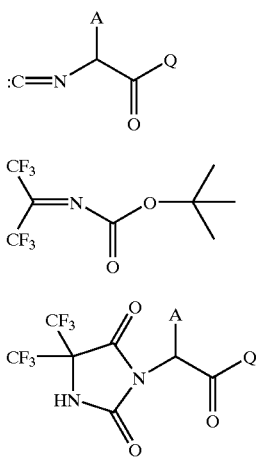

where A and Q have the meanings indicated above. For example, the group C(=O)—Q is an ester group and Q is alkoxy, such as $(C_1-C_4)$-alkoxy (e.g., methoxy, ethoxy and tert-butoxy) or $(C_6-C_{14})$-aryl-$(C_1-C_4)$-alkoxy (e.g., benzyloxy). The reaction of the compounds of formulae XXIII and XXIV to give the compounds of formula XXV is advantageously carried out in a hydrocarbon or ether as a solvent, for example in benzene or toluene, with warming, for example, to temperatures of from about 40° C. to about 80° C., for example to about 60° C.

The isonitriles (isocyanides) of formula XXIII can be obtained from the corresponding amino carboxylic acid esters of the formula $H_2N$—CHA—C(=O)—Q, wherein A and Q have the meanings indicated above, using standard methods known to one of ordinary skill in the art. Advantageously, the amino carboxylic acid ester of the formula $H_2N$—CHA—C(=O)—Q initially is converted into the N-formylamino acid ester of the formula HC(=O)—NH—CHA—C(=O)—Q by reaction with a reactive formic acid ester (e.g., cyanomethyl formate), which then is converted, for example, by reaction with phosgene or a phosgene equivalent (e.g., diphosgene or triphosgene) in the presence of a tertiary amine (e.g., triethylamine) into the isocyanide of formula XXIII. The 2-tert-butoxy-4,4-bis(trifluoromethyl)-1,3-oxazabuta-1,3-diene of formula XXIV is obtainable, according to the process described by Steglich et al., *Chemische Berichte*, 107:1488 (1974), from tert-butyl carbamate $((CH_3)_3C$—O—CO—$NH_2)$ and anhydrous hexafluoroacetone, and subsequent treatment of the initially obtained 2-tert-butoxycarbonylamino-2-hydroxy-1,1,1,3,3,3-hexafluoropropane with trifluoroacetic anhydride in the presence of a base, such as quinoline.

The compounds of formula XXV then can be alkylated, for example, with compounds of formula VII, at the NH group to give compounds of formula XIV. If desired, the ester group CO—Q in the compounds of formula XIV may be converted into the carboxylic acid group CO—OH, and further reacted with compounds of formula III to yield compounds of formula I as described above. In the compounds of formula XXV, it is also possible to convert the ester group CO—Q into the carboxylic acid group CO—OH using standard processes known to one of ordinary skill in the art and further to convert the obtained compound of formula XXII, as described above, into a compound of formula IIa by reacting the compound of formula XXII with an alkylating reagent of formula VII in the presence of excess base. The compound of formula IIa may be reacted with a compound of formula III to yield a compound of formula I. The 4-(3-arylureido)benzyl group or 4-(3-arylthioureido)benzyl group also can be introduced stepwise into the compounds of formula XXV using a process analogous to the preparation of the compounds of formula VIII described above and the compounds of formula II or IIa obtained therefrom. Functional groups can be present in protected form or in the form of precursors in this synthetic process.

The compounds of formula I, wherein E, for example, is hydroxycarbonyl or hydroxymethyl, can be converted into compounds of formula I, wherein E has other meanings, or into other prodrugs or derivatives of the compounds of formula I using standard methods known to one of ordinary skill in the art. Thus, the compounds of formula I, wherein E is hydroxycarbonyl, can be esterified using the appropriate alcohols (e.g., in the presence of a condensing reagent, such as DCC) to form the corresponding ester. In addition the compounds of formula I, wherein E is hydroxycarbonyl, can be alkylated with alkyl halides (e.g., alkyl chlorides or alkyl bromides), such as acyloxyalkyl halides, to give compounds of formula I, wherein E is acyloxyalkoxy-CO—. Compounds of formula I, wherein E is hydroxycarbonyl, can be converted into amides using ammonia or organic amines in the presence of a condensing reagent. In addition, compounds of formula I, wherein E is CO—$NH_2$, advantageously can be obtained on the solid phase by coupling the compound, wherein E is COOH, in the presence of a condensing agent, such as TOTU to Rink amide resin, and then removing it from the resin by treating with trifluoroacetic acid. Compounds of formula I, wherein E is the hydroxymethyl group, $CH_2OH$ can be etherified on the hydroxymethyl group using methods known to those of ordinary skill in the art. Compounds of formula I, wherein E is $CH_2OH$, can be converted into compounds of formula I, wherein E is the aldehyde group —CO—H, using methods known to those of ordinary skill in the art that pertain to the selective oxidation of alcohols to aldehydes, for example using sodium hypochlorite in the presence of 4-acetamido-2,2,6,6-tetramethylpiperidin-1-oxyl (4-acetamido-TEMPO).

Compounds of formula I, wherein $R^5$ is hydrogen also can be prepared by carrying out an ether cleavage with compounds of formula I, wherein $R^5$ is methyl. For example, a methoxy group representing $R^5O$ can be converted into a hydroxyl group by treatment with boron tribromide.

The compounds of formula I are valuable pharmaceutical active compounds that are suitable, for example, for the treatment of inflammatory diseases, allergic diseases or asthma. The compounds of formula I and their physiologically acceptable salts and derivatives can be administered to animals, preferably mammals, and more preferably humans, as pharmaceuticals for the treatment of disease conditions. The term treatment is generally understood to mean both the therapy of acute or chronic disease symptoms, as well as the prophylaxis or prevention of disease symptoms, i.e., for example, the prevention of acute allergic or asthmatic disease symptoms or the prevention of myocardial infarct or of myocardial reinfarct in appropriate patients. The compounds of formula I and their salts and derivatives can be administered on their own, in mixtures with one another or in the form of pharmaceutical preparations, which allow enteral or parenteral administration and which comprise an efficacious dose of at least one compound of formula I and/or its physiologically acceptable salts and/or derivatives and a pharmaceutically acceptable carrier.

The present invention also relates to the compounds of formula I and/or their physiologically acceptable salts and/or derivatives for use as pharmaceuticals (or as medicaments), the preparation of such pharmaceuticals, and their use in the treatment of the diseases mentioned above or below. The present invention further relates to pharmaceutical preparations (or pharmaceutical compositions) that contain an efficacious dose of at least one compound of formula I and/or its physiologically acceptable salts and/or derivatives and a pharmaceutically acceptable carrier (i.e., one or more pharmaceutically innocuous vehicles and/or additives).

The pharmaceuticals and pharmaceutical preparations can be administered systemically or locally. For example, the pharmaceuticals or pharmaceutical preparations can be administered orally in form of pills, tablets, film-coated tablets, sugar-coated tablets, granules, hard and soft gelatin capsules, powders, solutions, syrups, emulsions, suspensions or in other pharmaceutical forms. Administration, however, also can be carried out vaginally or rectally (e.g., in the form of suppositories), or parenterally or as implants (e.g., in the form of injection solutions or infusion solutions, microcapsules or rods), or topically or percutaneously (e.g., in the form of creams, ointments, powders, solutions, emulsions or tinctures), or by other methods known to one of ordinary skill in the art (e.g., in the form of nasal sprays or aerosol mixtures). Parenteral administration of solutions can occur, for example, intravenously, intramuscularly, subcutaneously, intra-articularly, intrasynovially or by other methods known to one of ordinary skill in the art.

The pharmaceutical preparations according to the invention are produced in a manner known per se, wherein the compound or the compounds of formula I and/or their physiologically acceptable salts and/or derivatives are mixed with pharmaceutically inert inorganic and/or organic vehicles and/or additives and prepared into a suitable dosage form and administration form. For the production of pills, tablets, sugar-coated tablets and hard gelatin capsules, it is possible to use, for example, lactose, cornstarch or derivatives thereof, talc, stearic acid or its salts, polyethylene glycols, etc., for soft gelatin capsules and suppositories, for example, fats, waxes, semisolid and liquid polyols, polyethylene glycols, natural or hardened oils etc. Suitable vehicles for the preparation of solutions (e.g., injection solutions, emulsions or syrups) are, for example, water, alcohols, glycerol, diols, polyols, sucrose, invert sugar, glucose, vegetable oils etc. and the like. Suitable vehicles for microcapsules, implants or rods are, for example, copolymers of glycolic acid and lactic acid. The pharmaceutical preparations normally contain from about 0.5 to about 90% by weight of the compounds of formula I and/or their physiologically acceptable salts and/or derivatives. The amount of active compound of formula I and/or its physiologically acceptable salts and/or derivatives in the pharmaceutical preparations is normally from about 0.2 mg to about 1000 mg, preferably from about 1 mg to about 500 mg. Depending on the nature of the pharmaceutical preparation, the amount of the active compound, however, also can be greater.

In addition to the active compounds and vehicles, the pharmaceutical preparations can also contain excipients or additives, for example, fillers, disintegrants, binders, lubricants, wetting agents, stabilizers, emulsifiers, preservatives, sweeteners, colorants, flavorings, aromatizers, thickening agents, diluents, buffer substances, solvents, solubilizers, agents for achieving a depot effect, salts for changing the osmotic pressure, coating agents or antioxidants. The pharmaceutical preparations can also contain two or more compounds of formula I and/or their physiologically acceptable salts and/or derivatives. In addition, the pharmaceutical preparations further can contain one or more other pharmaceutical active compounds, for example, substances having anti-inflammatory action.

The compounds of formula I or pharmaceutical preparations comprising them can be administered as aerosols (e.g., nasal aerosols or by inhalation) by using, for example, a spray, a nebulizer, a pump nebulizer, an inhalation apparatus, a metered inhaler or a dry powder inhaler. Pharmaceutical forms for administration as an aerosol can be prepared according to processes well known to one of ordinary skill in the art. For example, solutions or dispersions of the compounds of formula I in water, water/alcohol mixtures or suitable saline solutions can be employed using customary additives (e.g., benzyl alcohol or other suitable preservatives, absorption enhancers for increasing the bioavailability, solubilizers, dispersants and others), and, if appropriate, customary propellants (e.g., chlorofluorocarbons and/or fluorocarbons).

Other pharmaceutical active compounds which can be contained in the pharmaceutical preparations according to the invention in one or more pharmaceutical preparations in addition to compounds of formula I, but with which the compounds of formula I can also be combined in other ways in the context of a combination treatment are in particular those active compounds which are suitable for the treatment, i.e., the therapy or prophylaxis, of the diseases mentioned above or below for whose treatment the compounds of formula I are suitable. The classes of the other pharmaceutically active compounds that are different from formula I include, for example, steroids, nonsteroidal antiinflammatory substances, nonsteroidal antiinflammatory acetic acid derivatives, nonsteroidal antiinflammatory propionic acid derivatives, nonsteroidal antiasthmatics, salicylic acid derivatives, pyrazolones, oxicams, leukotriene antagonists, inhibitors of leukotriene biosynthesis, cyclooxygenase inhibitors, cyclooxygenase-2 inhibitors (COX-2 inhibitors), antihistamines, H1-histamine antagonists, nonsedating antihistamines, gold compounds, $\beta 2$ agonists, anticholinergics, muscarine antagonists, lipid-lowering agents, cholesterol-lowering agents, HMG-CoA reductase inhibitors, statins, nicotinic acid derivatives, immunosuppressants, cyclosporins, $\beta$-interferons, tumor therapeutics, cytostatics, metastasis inhibitors, antimetabolites, 5-aminosalicylic acid derivatives, antidiabetics, insulins, sulfonylureas, biguanides, glitazones, $\alpha$-glucosidase inhibitors, and others. Examples of suitable active compounds are acetylsalicylic acid, benorilate, sulfasalazine, phenylbutazone, oxyphenbutazone, metamizole, mofebutazone, feprazone, celecoxib, rofecoxib, diclofenac, fentiazac, sulindac, zomepirac, tolmetin, indometacin, acemetacin, ibuprofen, naproxen, carprofen, fenbufen, indoprofen, ketoprofen, pirprofen, tiaprofen acid, diflunisal, flufenamic acid, meclofenamic acid, mefenamic acid, niflumic acid, tolfenamic acid, piroxicam, isoxicam, tenoxicam, nicotinic acid, prednisone, dexamethasone, hydrocortisone, methylprednisolone, betamethasone, beclomethasone, budesonide, montelukast, pranlukast, zafirlukast, zileuton, ciclosporin, cyclosporin A, rapamycin, tacrolimus, methotrexate, 6-mercaptopurine, azathioprine, interferon-beta-1a, interferon-beta-1b, 5-aminosalicylic acid, leflunomide, D-penicillamine, chloroquine, glibenclamide, glimepiride, troglitazone, metformin, acarbose, atorvastatin, fluvastatin, lovastatin, simvastatin, pravastatin, colestipol, colestyramine, probucol, clofibrate, fenofibrate, bezafibrate, gemfibrozil, ipatropium bromide, clenbuterol, fenoterol, metaproterenol, pirbuterol, tulobuterol, salbutamol, salmeterol, terbutaline, isoetharine, ketotifen, ephedrine, oxitropium bromide, atropine, cromoglycic acid, theophylline, fexofenadine, terfenadine, cetirizine, dimetindene, diphenhydramine, diphenylpyraline, pheniramine, brompheniramine, chlorpheniramine, dexchlorpheniramine, alimezain, antazoline, astemizole, azatadine, clemastine, cyproheptadine, hydroxyzine, loratidine, mepyramine, promethazine, tripelennamine, triprolidine and others.

In combination treatments, the administration of compounds of formula I together with one or more other active compounds can be carried out by administering all active compounds together in a single pharmaceutical preparation (e.g., a tablet or capsule). The present invention also relates to pharmaceutical preparations of this type, for which all explanations above correspondingly apply. The amount of the active compounds in these pharmaceutical preparations generally is chosen to contain an efficacious amount of each active compound. A combination treatment, however, also can be carried out by administering the active compounds in two or more separate pharmaceutical preparations, which can be present in a single unit or in two or more separate units. The administration of the compounds of formula I and the other active compounds can be carried out jointly or separately, as well as simultaneously or successively, in any order. The administration also can be carried out using more than one method known to one of ordinary skill in the art, for example, one active compound can be administered orally and the other by injection, inhalation or topical application. All such treatments are encompassed by the present invention.

The compounds of formula I, for example, have the ability to inhibit cell-cell interaction processes and cell-matrix interaction processes, wherein interactions between VLA-4 and its ligands play a role. The activity of the compounds of formula I can be demonstrated, for example, in an assay, wherein the binding of cells, which contain the VLA-4 receptor (e.g., of leukocytes), to ligands of this receptor is measured (e.g., to VCAM-1), which for this purpose can advantageously also be prepared by genetic engineering. Details of such assays are described below. In particular, the compounds of formula I have the ability to inhibit the adhesion and the migration of leukocytes (e.g., the adhesion of leukocytes to endothelial cells), which is controlled by the VCAM-1/VLA-4 adhesion mechanism, as explained above. In addition to being active antiinflammatories, the compounds of formula I and their physiologically tolerable salts and derivatives are generally suitable for the treatment (i.e., for the therapy and prophylaxis) of diseases that are based on the interaction between the VLA-4 receptor and its ligands or can be influenced by an inhibition of this interaction. In particular, the compounds of formula I are suitable for the treatment of diseases that are caused at least partly by an undesired extent of leukocyte adhesion and/or leukocyte migration or are connected therewith, and for whose prevention, alleviation or cure the adhesion and/or migration of leukocytes should be decreased.

The present invention also relates to the compounds of formula I and/or their physiologically acceptable salts and/or derivatives for the inhibition of the adhesion and/or migration of leukocytes or for the inhibition of the VLA4 receptor. In addition, the present invention relates to the use of the compounds of formula I and/or their physiologically acceptable salts and/or derivatives for the preparation of pharmaceuticals thereof, i.e., of pharmaceuticals for the treatment of diseases, wherein the leukocyte adhesion and/or leukocyte migration shows an undesired extent, or for the treatment of diseases, wherein VLA-4-dependent adhesion processes play a role, and to the use of the compounds of formula I and/or their physiologically acceptable salts and/or derivatives in the treatment of diseases of this type.

The compounds of formula I can be employed as antiinflammatories, in the case of inflammatory symptoms of very different cause, to prevent, reduce or suppress the undesired or harmful sequelae of the inflammation. They are used, for example, for the treatment of arthritis, rheumatoid arthritis, polyarthritis, inflammatory bowel disease (ulcerative colitis, Crohn's disease), systemic lupus erythematosus, inflammatory diseases of the central nervous system (e.g., multiple sclerosis), or asthma or allergies (e.g., allergies of the delayed type (type IV allergy)). Furthermore, compounds of formula I are suitable for cardioprotection, for stroke protection and for the secondary prophylaxis of stroke and for the treatment of cardiovascular diseases, atherosclerosis, myocardial infarct, myocardial reinfarct, acute coronary syndrome, stroke, restenoses, diabetes, damage to organ transplants, immune diseases, autoimmune diseases, tumor growth or tumor metastasis in various malignancies, malaria and other diseases where a blocking of the integrin VLA-4 and/or an influencing of the leukocyte activity appears appropriate for prevention, alleviation or cure. A preferred use is the prevention of myocardial infarct or of myocardial reinfarct.

The dosage amounts of the compounds of formula I can vary within wide limits and is to be adjusted in each individual case in view of the individual conditions, as readily determined by those skilled in the art (e.g., physicians). Thus, the magnitude of a prophylactic or therapeutic dose of the compounds of formula I depends, for example, on the nature and severity of the disease to be treated, the condition of the patient, the compound employed, whether an acute or chronic disease condition is being treated or prophylaxis is conducted, or whether, in addition to the compounds of formula I, further active compounds may be administered. In general, oral administration of a daily dose from about 0.01 to about 100 mg/kg, preferably from about 0.1 to about 10 mg/kg (in each case mg per kg of body weight) is adequate for administration to an adult weighing about 75 kg to achieve efficacious results. For intravenous administration, the daily dose in general is from about 0.01 to about 50 mg/kg, preferably from about 0.01 to about 10 mg/kg (in each case mg per kg of body weight). The daily dose can be divided into a number of partial administrations (e.g., 2, 3, or 4), particularly in the administration of relatively large amounts. If appropriate, it may be necessary to decrease or increase the daily dose indicated, depending on individual behavior.

In addition to being pharmaceutically active compounds in human medicine and veterinary medicine, the compounds of formula I and their salts and derivatives can further be employed for diagnostic purposes (e.g., in in vitro diagnoses of cell samples or tissue samples), and as an auxiliary or as a scientific tool in biochemical investigations, wherein a blocking of VLA-4 or an influencing of cell-cell or cell-matrix interactions is desired. Furthermore, the compounds of formula I and their salts can be used as intermediates for the preparation of other compounds, particularly other pharmaceutical active compounds, which are obtainable from compounds of formula I (e.g., by modification or introduction of residues or functional groups, such as by esterification, reduction, oxidation or other transformations of functional groups).

EXAMPLES

Example 1
(R)-3-((S)-2-(4,4-Dimethyl-3-(4-(3-(2-methylphenyl) ureido)-3-methoxybenzyl)-2,5-dioxoimidazolidin-1-yl)-2-(cyclopropylmethyl)acetylamino)-3-methylpropionic Acid

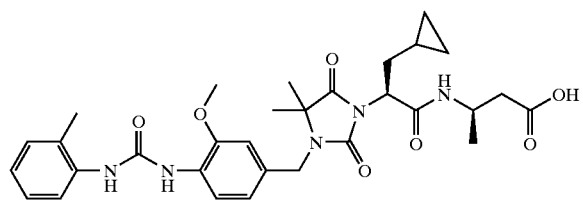

1a) 4-(3-(2-Methylphenyl)ureido)-3-methoxybenzyl Alcohol 15 g (81.8 mmol) of 3-methoxy-4-nitrobenzyl alcohol were hydrogenated over 1.3 g of palladium/carbon (10% strength; 50% water) in 500 mL of methyl tert-butyl ether with ice cooling. After the absorption of hydrogen was complete, the catalyst was filtered off and 10.14 mL (81.8 mmol) of 2-methylphenyl isocyanate were added to the filtrate with stirring in the course of 30 minutes. The reaction mixture was allowed to stand overnight, and the precipitated solid was filtered off with suction and washed with methyl tert-butyl ether. Yield: 20.5 g (88%).

1b) 4-(3-(2-Methylphenyl)ureido)-3-methoxybenzyl Chloride 7.65 mL (104.8 mmol) of thionyl chloride were added dropwise with ice cooling to a suspension of 15 g (52.4 mmol) of the compound of Example 1a in 300 mL of dichloromethane. The reaction mixture was stirred at room temperature for 3 hours, allowed to stand overnight and poured onto 1000 mL of heptane. The heptane was decanted off from the separated oil, the residue was suspended again in heptane and the heptane was decanted off. This process was repeated a further two times. The residue was then dissolved in dichloromethane and poured into 800 mL of ice-cold diisopropyl ether. The mixture was stirred for 2 hours with ice cooling, and the product was filtered off with suction, washed with diisopropyl ether and dried over phosphorus pentoxide. Yield: 12 g (75%).

1c) Benzyl (S)-2-amino-3-cyclopropylpropionate 1N sodium hydroxide solution was added at 0° C. to a suspension of 10 g (77.5 mmol) of (S)-2-amino-3-cyclopropylpropionic acid in 160 mL of dioxane until pH 8–9 was achieved. 16.9 g (77.5 mmol) of di-tert-butyl dicarbonate were then added, the ice bath was removed and the pH was kept at 8–9 by further addition of 1N sodium hydroxide solution. After allowing to stand overnight, the dioxane was removed in vacuo, ethyl acetate was added to the water phase and the phases were separated. The water phase was adjusted to pH 4.5 using 1N hydrochloric acid and extracted with ethyl acetate. The ethyl acetate phase obtained was dried over sodium sulfate, the sodium sulfate was filtered off and the filtrate was concentrated in vacuo. The residue was dissolved in 1000 mL of dichloromethane and treated with 53.4 mL of benzyl alcohol, 8.37 g of 4-dimethylaminopyridine and 18.8 g of DCC. After stirring for 6 hours and allowing to stand overnight, the mixture was filtered, the filtrate was concentrated and the residue was treated with 300 mL of 90% strength trifluoroacetic acid. After stirring at room temperature for 10 minutes, the trifluoroacetic acid was removed in vacuo and the residue was chromatographed twice over silica gel (dichloromethane/methanol, 95/5). Yield: 11.48 g (68%).

1d) (S)-2-(4,4-Dimethyl-2,5-dioxoimidazolidin-1-yl)-2-(cyclopropylmethyl)acetic Acid 321 mg of HOBT and 4.75 g (23.7 mmol) of DCC were added to a solution of 3.82 g (23.7 mmol) 2-methoxycarbonylamino-2-methylpropionic acid (prepared from 2-amino-2-methylpropionic acid and methyl chloroformate) and 5.2 g (23.7 mmol) of the compound of Example 1c in 100 mL of THF and the mixture was stirred at room temperature for 4 hours. After allowing to stand overnight and filtration, the THF was removed in vacuo, the residue was taken up in methyl tert-butyl ether and the solution was washed twice in each case with saturated $NaHCO_3$ solution and aqueous $KHSO_4/K_2SO_4$ solution. The organic phase was dried over sodium sulfate and, after filtration, the solvent was removed in vacuo. The residue was dissolved in ethyl acetate and hydrogenated in the presence of palladium/carbon (10% strength; 50% water). The catalyst was filtered off and 500 mL of water and 10.1 g of sodium carbonate were added to the organic phase. After extraction by shaking and phase separation, the water phase was stirred at 100° C. for 24 hours. After allowing to stand overnight, 500 mL of 6N hydrochloric acid were added and the water phase was extracted three times with methyl tert-butyl ether. The combined organic phases were dried over sodium sulfate and, after filtration, concentrated in vacuo. The residue was crystallized using diisopropyl ether and the product was filtered off. Yield: 2.88 g (51%).

1e) (S)-2-(4,4-Dimethyl-3-(4-(3-(2-methylphenyl)ureido)-3-methoxybenzyl)-2,5-dioxoimidazolidin-1-yl)-2-(cyclopropylmethyl)acetic Acid

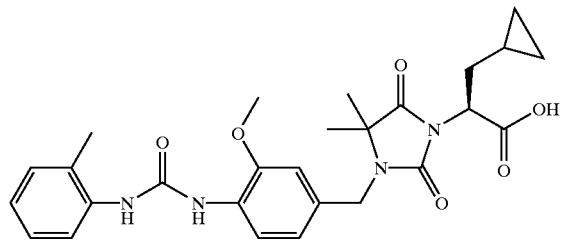

9.44 mL of an n-butyllithium solution (2.5M in hexane) were added at −40° C. under argon to a solution of 2.85 g (11.8 mmol) of the compound of Example 1d in 60 mL of absolute THF. After stirring at −40° C. for 30 minutes, the reaction mixture was allowed to warm to 0° C. and a solution of 3.6 g (11.8 mmol) of the compound of Example 1b in 20 mL of N-methyl-2-pyrrolidone was added. The reaction mixture was allowed to warm to 0° C. and then stirred for 2 hours at 0° C. 15 mL of 1N hydrochloric acid were added and the THF was removed in vacuo. The residue was poured onto 300 mL of methyl tert-butyl ether. The phases were separated, and the organic phase was washed with water, dried over sodium sulfate and, after filtration, concentrated in vacuo. The residue was purified by preparative HPLC. After concentration of the product fractions and freeze drying, 1.33 g (22%) of the title compound were obtained.

1f) tert-Butyl (R)-3-((S)-2-(4,4-dimethyl-3-(4-(3-(2-methylphenyl)ureido)-3-methoxy-benzyl)-2,5-dioxoimidazolidin-1-yl)-2-(cyclopropylmethyl)acetylamino)-3-methylpropionate 626 mg (1.91 mmol) of TOTU and 308 μL (1.81 mmol) of N,N-diisopropylethylamine were added successively with ice cooling to a solution of 974 mg (1.91 mmol) of the compound of Example 1e and 305 mg (1.91 mmol) of tert-butyl (R)-3-amino-butanoate in 10 mL of absolute DMF. After stirring at room temperature for 2 hours, the solvent was removed in vacuo, the residue was dissolved in ethyl acetate and the ethyl acetate solution was washed successively twice in each case with an aqueous KHSO$_4$/K$_2$SO$_4$ solution, a saturated NaHCO$_3$ solution and water. After drying the organic phase over sodium sulfate and filtration, the solvent was removed in vacuo and the residue was chromatographed over silica gel using ethyl acetate/heptane (1/1). After concentration of the product fractions, 880 mg (71%) of the title compound were obtained.

1g) (R)-3-((S)-2-(4,4-Dimethyl-3-(4-(3-(2-methylphenyl)ureido)-3-methoxybenzyl)-2,5-dioxoimidazolidin-1-yl)-2-(cyclopropylmethyl)acetylamino)-3-methylpropionic Acid 880 mg (1.35 mmol) of the compound of Example 1f were treated with 10 mL of 90% strength trifluoroacetic acid. After 15 minutes at room temperature, the reaction mixture was concentrated in vacuo. The residue was taken up in dichloromethane and concentrated in vacuo. This process was repeated a second time. The residue obtained then was taken up in dichloromethane, and the dichloromethane phase was washed three times with water and dried over sodium sulfate. After filtration and concentration in vacuo, the residue was taken up in acetonitrile/water and freeze dried. Yield: 730 mg (91%).

ES(+)-MS: 594.2 (M+H)$^+$

Example 2

(R)-3-((S)-2-(4,4-Dimethyl-3-(4-(3-(2-methylphenyl)ureido)-3-methoxybenzyl-2,5-dioxoimidazolidin-1-yl)-2-(cyclopropylmethyl)acetylamino)-3-methylpropionic Acid Sodium Salt

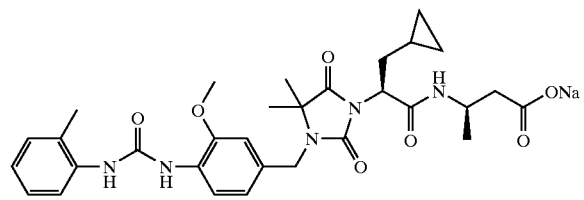

1.64 mL of 0.1N sodium hydroxide solution were added in portions with stirring to a suspension of 100 mg (0.168 mmol) of the compound of Example 1 in 10 mL of water and the mixture was stirred at room temperature for 1 hour. After filtering and freeze drying the filtrate, 104 mg (100%) of the title compound were obtained.

ES(+)-MS: 594.3
((R)-3-((S)-2-(4,4-dimethyl-3-(4-(3-(2-methylphenyl)ureido)-3-methoxybenzyl)-2,5-diox oimidazolidin-1-yl)-2-(cyclopropylmethyl)acetylamino)-3-methylpropionic Acid+H)$^+$, 616.2 (M$^+$).

Example 3

(R)-3-((S)-2-(4,4-Dimethyl-3-(4-(3-(2-methylphenyl)ureido)-3-methoxybenzyl)-2,5-dioxoimidazolidin-1-yl)-2-(cyclopropylmethyl)acetylamino)-3-methylpropanol

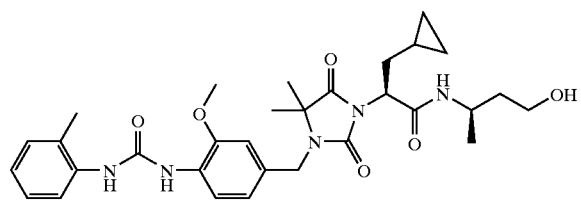

535 mg (1.05 mmol) of the compound of Example 1e in 15 mL of absolute DMF were treated with ice cooling with 140 mg (1.05 mmol) of HOBT and 260 mg (1.26 mmol) of DCC. The mixture was stirred for 45 minutes with ice cooling, then 112 mg (1.26 mmol) of (R)-3-amino-3-methylpropanol were added and the mixture was stirred at room temperature for 2 hours. After allowing to stand overnight, the mixture was filtered, the filtrate was concentrated, the residue was dissolved in ethyl acetate and the ethyl acetate phase was washed twice with aqueous KHSO$_4$/K$_2$SO$_4$ solution. After drying over sodium sulfate, filtering and concentrating, the residue was chromatographed over silica gel using ethyl acetate. After concentrating the product fractions, 423 mg (70%) of the title compound were obtained.

ES(+)-MS: 580.3 (M+H)$_+$

Preparation of (R)-3-amino-3-methylpropanol 5.68 g (149 mmol) of lithium aluminum hydride were added in portions under argon to a solution of 19.9 g (149 mmol) of aluminum trichloride in 250 mL of absolute diethyl ether and the mixture was heated under reflux for 30 minutes. 6 g (37.7 mmol) of tert-butyl (R)-3-aminobutanoate in 50 mL of absolute diethyl ether were slowly added dropwise and the reaction mixture was heated under reflux for 2 hours. 10.8 mL of water and 25.3 g of potassium hydroxide, dissolved in 43 mL of water, were then added dropwise cautiously with ice cooling. The mixture was allowed to stand overnight at room temperature, the ether phase was decanted off and the residue was boiled three times with dichloromethane. The combined organic phases were dried over sodium sulfate. After filtration and removal of the solvent in vacuo, 2.5 g (75%) of the title compound were obtained.

Example 4

(R)-3-((S)-2-(4,4-Dimethyl-3-(4-(3-(2-methylphenyl)ureido)-3-methoxybenzyl)-2,5-dioxoimidazolidin-1-yl)-2-(cyclopropylmethyl)acetylamino)-3-methylpropionamide

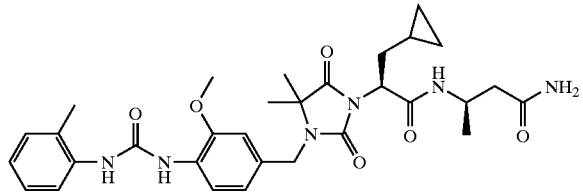

131 mg (0.636 mmol) of DCC were added to a solution of 330 mg (0.555 mmol) of the compound of Example 1 and 125 mg (0.926 mmol) of HOBT in 4 mL of absolute DMF, the mixture was stirred at room temperature for 1 hour and then 47 μL (0.555 mmol) of a 25% strength aqueous ammonia solution were added. The mixture was allowed to stand overnight at room temperature, a further 16 μL of a 25% strength aqueous ammonia solution were added and the mixture was stirred for 4 hours. After filtration, the filtrate was concentrated in vacuo, the residue was dissolved in ethyl acetate and the ethyl acetate phase was washed twice in each case with an aqueous KHSO₄/K₂SO₄ solution, a saturated NaHCO₃ solution and water. After drying the organic phase over sodium sulfate and filtering, the solvent was removed in vacuo and the residue was chromatographed over silica gel using ethyl acetate. After concentrating the product fractions and freeze drying, 272 mg (82%) of the title compound were obtained.

ES(+)-MS: 593.3

Example 5

(R)-3-((S)-2-(4,4-Dimethyl-3-(4-(3-(2-methylphenyl)ureido)-3-hydroxybenzyl)-2,5-dioxoimidazolidin-1-yl)-2-(cyclopropylmethyl)acetylamino)-3-methylpropionic Acid

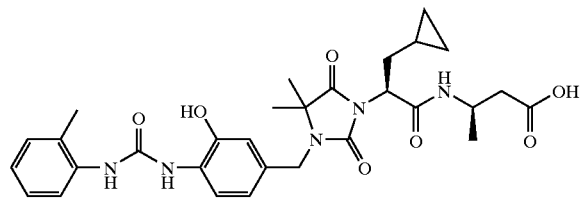

211 μL of boron tribromide were added under argon to a solution of 100 mg (0.169 mmol) of the compound of Example 1 in 20 mL of absolute dichloromethane at −78° C. and the reaction mixture was allowed to warm to 0° C. with ice cooling. After 30 minutes at 0° C., water was cautiously added. The phases were separated and the organic phase was dried over sodium sulfate. After filtration, removal of the solvent in vacuo, chromatographic purification by preparative HPLC and freeze drying of the product fractions, 35 mg (36%) of the title compound were obtained.

ES(+)-MS: 580.2 (M+H)₊

Example 6

(R)-3-((S)-2-(4,4-Dimethyl-3-(4-(3-(2-methylphenyl)ureido)-3-hydroxybenzyl)-2,5-dioxoimidazolidin-1-yl)-2-(cyclopropylmethyl)acetylamino)-3-methylpropanol

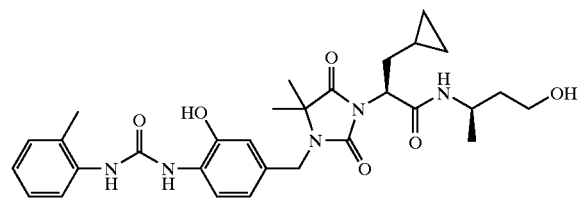

488 μL of boron tribromide were added under argon to a solution of 220 mg (0.39 mmol) of the compound of Example 3 in 40 mL of absolute dichloromethane at −78° C. and the reaction mixture was allowed to warm to 0° C. with ice cooling. After 30 minutes at 0° C., water was cautiously added. The phases were separated, and the organic phase was washed four times with water and dried over sodium sulfate. After filtration, removal of the solvent in vacuo, chromatographic purification by preparative HPLC and freeze drying of the product fractions, 81 mg (37%) of the title compound were obtained.

ES(+)-MS: 566.3 (M+H)₊

Example 7

(R)-3-((S)-2-(4,4-Dimethyl-3-(4-(3-phenylureido)-3-methoxybenzyl)-2,5-dioxoimidazolidin-1-yl)-2-(cyclopropylmethyl)acetylamino)-3-methylpropionic Acid

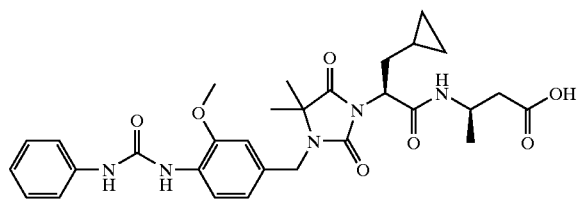

7a) 4-(3-Phenylureido)-3-methoxybenzyl chloride 7.55 mL (103.4 mmol) of thionyl chloride were added dropwise to a suspension of 14.07 g (51.7 mmol) of 4-(3-phenylureido)-3-methoxybenzyl alcohol (prepared as described in Example 1, phenyl isocyanate being employed instead of 2-methylphenyl isocyanate) in 200 mL of dichloromethane. The mixture then was stirred at room temperature for 2 hours, allowed to stand overnight and poured onto 800 mL of heptane. The heptane was decanted off from the separated oil, the residue was suspended several times in heptane and in each case the heptane was decanted off. The residue was dissolved in 100 mL of dichloromethane and added dropwise to 800 mL of diisopropyl ether. The mixture was stirred for 1 hour with ice cooling, and the product was filtered off with suction, washed with diisopropyl ether and dried in vacuo.

7b) (S)-2-(4,4-Dimethyl-3-(4-(3-phenylureido)-3-methoxybenzyl)-2,5-dioxoimidazolidin-1-yl)-2-(cyclopropylmethyl)acetic Acid

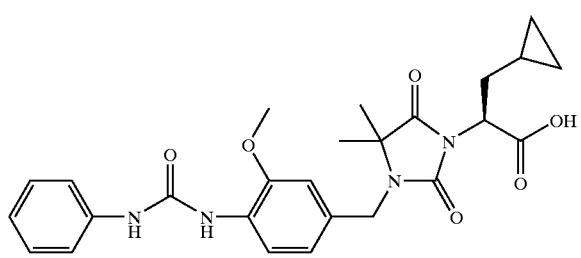

9.32 mL of an n-butyllithium solution (2.5M in hexane) were added at −40° C. under argon to a solution of 2.8 g (11.6 mmol) of the compound of Example 1d in 60 mL of absolute THF. After stirring at −40° C. for 30 minutes, the reaction mixture was allowed to warm to 0° C. and a solution of 5.07 g (17.4 mmol) of the compound of Example 7a in 20 mL of N-methyl-2-pyrrolidone was added. The reaction mixture was allowed to warm to 0° C. and it was then stirred for 2 hours at 0° C. 15 mL of 1N hydrochloric acid were added, the THF was removed in vacuo and the residue was poured onto 300 mL of methyl tert-butyl ether. The phases were separated, and the organic phase was washed with water, dried over sodium sulfate and, after filtration, concentrated in vacuo. The residue was purified by preparative HPLC. After concentration of the product fractions and subsequent freeze drying, 484 mg (8%) of the title compound were obtained.

7c) (R)-3-((S)-2-(4,4-Dimethyl-3-(4-(3-phenylureido)-3-methoxybenzyl-2,5-dioxoimidazolidin-1-yl)-2-(cyclopropylmethyl)acetylamino)-3-methylpropionic acid The compound was obtained analogously to Example 1 from 120 mg (0.242 mmol) of the compound of Example 7b and 38 mg (0.242 mmol) of tert-butyl (R)-3-aminobutanoate by coupling, chromatographic purification, cleavage of the tert-butyl ester and freeze drying. Yield: 113 mg (81%).

ES(+)-MS: 580.2 (M+H)+

Example 8

(R)-3-((S)-2-(4,4-Dimethyl-3-(4-(3-phenylureido)-3-methoxybenzyl-2,5-dioxoimidazolidin-1-yl)-2-(cyclopropylmethyl)acetylamino)-3-methylpropanol

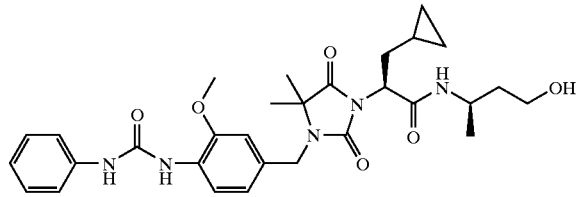

The compound was prepared analogously to Example 3 from 172 mg (0.348 mmol) of the compound of Example 7b and 31 mg (0.417 mmol) of (R)-3-amino-3-methylpropanol (see Example 3) by coupling, chromatographic purification (ethyl acetate/heptane, 9/1), concentration of the product fractions and freeze drying. Yield: 117 mg (59%).

ES(+)-MS: 566.3 (M+H)+

Example 9

Ethyl 3-((S)-2-(4,4-dimethyl-3-(4-(3-(2-methylphenyl)ureido)-3-methoxybenzyl)-2,5-dioxoimidazolidin-1-yl)-2-(cyclopropylmethyl)acetylamino)-3-(3-pyridyl)propionate

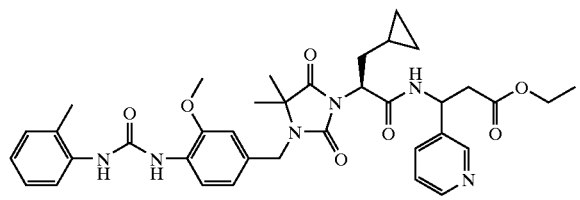

129 mg (0.393 mmol) of TOTU and 64 μL (0.374 mmol) of N,N-diisopropylethylamine were added with ice cooling to a solution of 200 mg (0.393 mmol) of the compound of Example 1d and 76.4 mg (0.393 mmol) of ethyl 3-amino-3-(3-pyridyl)propionate (for preparation see J. G. Rico et al., *J. Org. Chem.*, 58: 7948 (1993)) in 5 mL of absolute DMF. After stirring at room temperature for 30 minutes, the solvent was removed in vacuo and the residue was taken up in ethyl acetate. The ethyl acetate solution was washed successively twice in each case with a saturated NaHCO3 solution and water. After drying the organic phase over sodium sulfate and filtering, the solvent was removed in vacuo and the residue was chromatographed over silica gel using ethyl acetate. After concentrating the product fractions, 195 mg (72%) of the title compound were obtained.

ES(+)-MS: 685.4 (M+H)+

Example 10

3-((S)-2-(4,4-Dimethyl-3-(4-(3-(2-methylphenyl)ureido)-3-methoxybenzyl)-2,5-dioxoimidazolidin-1-yl)-2-(cyclopropylmethyl)acetylamino)-3-(3-pyridyl)propionic Acid Hydrochloride

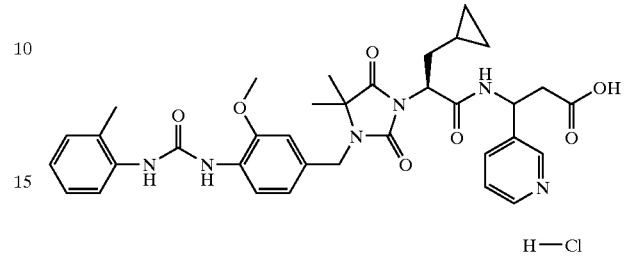

0.82 mL (0.82 mmol) of a 1 M aqueous lithium hydroxide solution was added to a solution of 141 mg (0.206 mmol) of the compound of Example 9 in 7.25 mL of methanol and the reaction mixture was allowed to stand overnight at room temperature. The methanol was then removed in vacuo, the residue was adjusted to pH 2 using 1N hydrochloric acid and the mixture was concentrated in vacuo. The residue was chromatographed over silica gel using dichloromethane/methanol/glacial acetic acid/water (95/5/0.5/0.5). After concentrating the product fractions, the residue was treated with 1.11 equivalents of 1N hydrochloric acid and freeze dried. Yield: 120 mg (89%).

ES(+)-MS: 657.4 (M+H)+

Example 11

Isopropyl 3-((S)-2-(4,4-dimethyl-3-(4-(3-(2-methylphenyl)ureido)-3-methoxybenzyl-2,5-dioxoimidazolidin-1-yl)-2-(cyclopropylmethyl)acetylamino)-3-(3-pyridyl)propionate

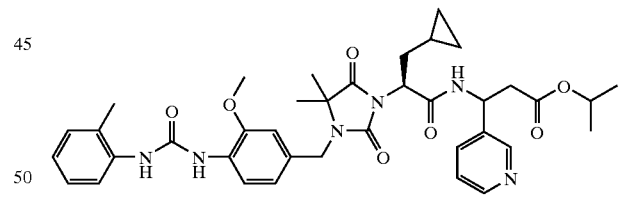

56 μL (0.731 mmol) of isopropanol and 23.6 mg (0.193 mmol) of 4-dimethylaminopyridine were added to a suspension of 80 mg (0.122 mmol) of the compound of Example 11 in 3 mL of dichloromethane. 38 mg (0.183 mmol) of DCC, dissolved in 1 mL of dichloromethane, were added to the then clear solution. After stirring at room temperature for 2 hours, the mixture was allowed to stand overnight at room temperature. After filtration, the filtrate was concentrated in vacuo and the residue was chromatographed over silica gel using heptane/ethyl acetate (3/1) and ethyl acetate/heptane (20/1). After concentrating the product fractions, 70 mg (82%) of the title compound were obtained.

ES(+)-MS: 699.4 (M+H)+

Example 12

Ethyl 3-((S)-2-(4,4-dimethyl-3-(4-(3-(2-methylphenyl)ureido)-3-methoxybenzyl-2,5-dioxoimidazolidin-1-yl)-2-(cycloproylmethyl)acetylamino)-3-(4-pyridyl)propionate

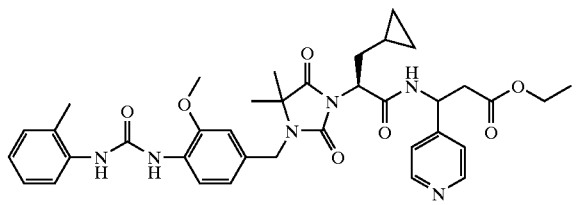

The compound was prepared analogously to Example 9 from 200 mg (0.393 mmol) of the compound of Example 1d and 76.4 mg (0.393 mmol) of ethyl 3-amino-3-(4-pyridyl)propionate (for preparation see J. G. Rico et al., *J. Org. Chem.*, 58:7948 (1993)). Yield: 199 mg (74%).

ES(+)-MS: 685.4 (M+H)$^+$

Example 13

3-((S)-2-(4,4-Dimethyl-3-(4-(3-(2-methylphenyl)ureido)-3-methoxybenzyl)-2,5-dioxoimidazolidin-1-yl)-2-(cyclopropylmethyl)acetylamino)-3-(4-pyridyl)propionic Acid Hydrochloride

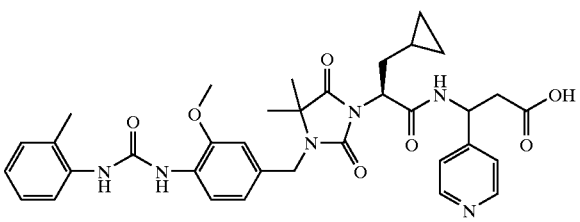

The compound was prepared analogously to Example 10 from 143 mg (0.209 mmol) of the compound of Example 12. Yield: 126 mg (87%).

ES(+)-MS: 657.2 (M+H)$^+$

Example 14

Isopropyl 3-((S)-2-(4,4-dimethyl-3-(4-(3-(2-methylphenyl)ureido)-3-methoxybenzyl)-2,5-dioxoimidazolidin-1-yl)-2-(cyclopropylmethyl)acetylamino)-3-(4-pyridyl)propionate

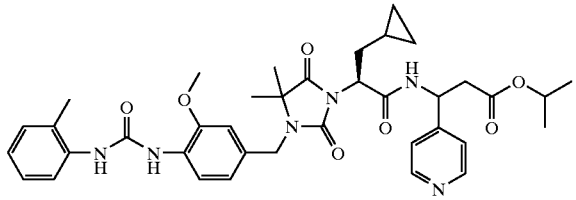

The compound was prepared analogously to Example 11 from 83 mg (0.126 mmol) of the compound of Example 13. Yield: 34.6 mg (39%).

ES(+)-MS: 699.4 (M+H)$^+$

Example 15

Ethyl 3-((S)-2-(4,4-dimethyl-3-(4-(3-(2-methylphenyl)ureido)-3-methoxybenzyl)-2,5-dioxoimidazolidin-1-yl)-2-(cyclopropylmethyl)acetylamino)-3-(2-pyridyl)propionate

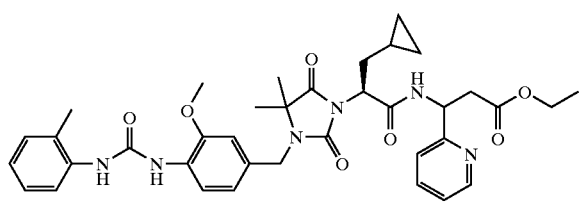

The compound was prepared analogously to Example 9 from 200 mg (0.393 mmol) of the compound of Example 1d and 76.4 mg (0.393 mmol) of ethyl 3-amino-3-(2-pyridyl)propionate (for preparation see J. G. Rico et al., J. Org. Chem. 58 (1993) 7948). Yield: 226 mg (84%).

ES(+)-MS: 685.4 (M+H)$^+$

Example 16

3-((S)-2-(4,4-Dimethyl-3-(4-(3-(2-methylphenyl)ureido)-3-methoxybenzyl)-2,5-dioxoimidazolidin-1-yl)-2-(cyclopropylmethyl)acetylamino)-3-(2-pyridyl)propionic Acid

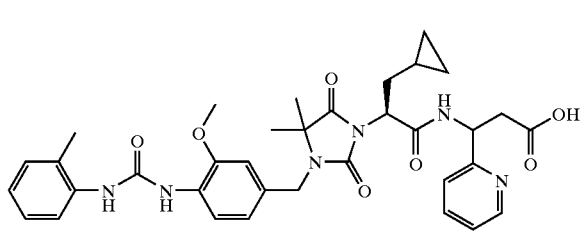

The compound was prepared analogously to Example 10 from 170 mg (0.248 mmol) of the compound of Example 15, but was not converted into the hydrochloride by addition of hydrochloric acid. Yield: 160 mg (98%).

ES(+)-MS: 657.4 (M+H)$^+$

Example 17

Isopropyl 3-((S)-2-(4,4-dimethyl-3-(4-(3-(2-methylphenyl)ureido)-3-methoxybenzyl)-2,5-dioxoimidazolidin-1 yl)-2-(cyclopropylmethyl)acetylamino)-3-(2-pyridyl)propionate

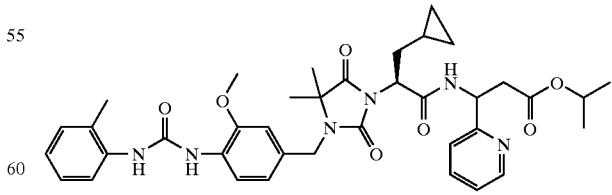

The compound was prepared analogously to Example 11 from 90 mg (0.137 mmol) of the compound of Example 16. Yield: 39 mg (41%).

ES(+)-MS: 699.4 (M+H)$^+$

Example 18
(R)-3-((S)-2-(4,4-Bis(trifluoromethyl)-3-(4-(3-(2-methylphenyl)ureido)-3-methoxybenzyl)-2,5-dioxoimidazolidin-1-yl)-2-(cyclopropylmethyl)acetylamino)-3-methylpropionic Acid

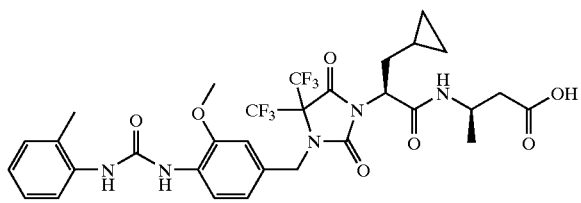

18a) 2-tert-Butoxy-4,4-bis(trifluoromethyl)-1,3-oxazabuta-1,3-diene

The compound was prepared analogously to W. Steglich et al., Chem. Ber, 107:1488–1498 (1974). For the preparation of anhydrous hexafluoroacetone (HFA), HFA trihydrate was added dropwise to concentrated sulfuric acid which had been warmed to 80° C. The resulting gas was washed once more with concentrated sulfuric acid and then passed into the gas space of the reaction flask. A reflux condenser filled with acetone/dry ice was fitted to the gas outlet of the flask.

As described above, a solution of 20 g (170 mmol) of tert-butyl carbamate in 150 mL of dichloromethane was reacted with anhydrous gaseous HFA until the reaction solution was saturated. The solvent was removed in vacuo and the resulting crude 2-tert-butoxycarbonylamino-2-hydroxy-1,1,1,3,3,3-hexafluoropropane (yield: 48.3 g, 100%) was used in the subsequent reaction step.

13.6 g of trifluoroacetic anhydride and subsequently 5 drops of quinoline were added dropwise at 0° C. to a solution of 50.05 g (176 mmol) of 2-tert-butoxycarbonylamino-2-hydroxy-1,1,1,3,3,3-hexafluoropropane in 300 mL of diethyl ether. After stirring at 0° C. for 10 minutes, a further 27.2 g of trifluoroacetic anhydride were added dropwise. The reaction mixture was stirred at 0° C. (external temperature) for 30 minutes, the internal temperature of the mixture rising to 8–10° C. After cooling to 0° C., 50.01 g (388 mmol) of quinoline were added, the trifluoroacetic acid salt of quinoline beginning to crystallize. After stirring at 0° C. for 2 hours, the mixture was filtered. Residual salt was removed from the filtrate by distilling it in vacuo into a receiver flask cooled with acetone/dry ice. The distillate was then distilled through a Vigreux column. 36.2 g (77%) of the title compound were obtained. Boiling point: 126–130° C.

18b) (S)-β-Cyclopropylalanine tert-butyl Ester 3.5 g (27.1 mmol) of (S)-β-cyclopropylalanine were added at room temperature to a mixture of 50 mL of dioxane and 5 mL of concentrated sulfuric acid (prepared by cautious dropwise addition of the acid to dioxane at 5° C.). The solution was transferred into a sealing tube into which 40 mL of isobutylene were condensed at −78° C. The sealed tube was then shaken at room temperature for 24 hours on a shaker. After opening of the sealed tube (with cooling), the reaction mixture was cautiously introduced into a stirred mixture, cooled to 0° C., of 30 mL of triethylamine and 50 mL of water. After removing excess isobutylene, the product was extracted with ether (2×50 mL). After drying the ether phases over magnesium sulfate, filtering and removing the solvent in vacuo, the crude product obtained (pale yellow oil) was employed in the subsequent reaction without further purification. Yield 4.2 g (84%). 18c) (S)—N-Formyl-β-cyclopropylalanine tert-butyl Ester A mixture of 10 g (54 mmol) of (S)-β-cyclopropylalanine tert-butyl ester and 4.7 g (55.2 mmol) of cyanomethyl formate in 100 mL of dichloromethane was stirred overnight at room temperature. After removing the solvent in vacuo, the residue obtained was distilled in vacuo. Yield: 8.8 g (76%). Boiling point 120° C./40 Pa (0.3 torr).

18d) tert-Butyl (S)-2-(4,4-bis(trifluoromethyl)-2,5-dioxoimidazolidin-1-yl)-2-(cyclopropylmethyl)acetate 2.4 g (12.1 mmol) of diphosgene were added at −30° C. to a solution of 2.5 g (11.7 mmol) of (S)—N-formyl-β-cyclopropylalanine tert-butyl ester and 2.5 g (24.7 mmol) of triethylamine in 100 mL of dry dichloromethane. The reaction solution was allowed to warm to −15° C. in the course of 1 hour and stirring was continued at this temperature until the reaction was complete. The reaction solution was then washed twice at room temperature with 7% strength sodium hydrogencarbonate solution and the organic phase was dried over magnesium sulfate. After filtration, the solvent was removed in vacuo and the residue was taken up in 70 mL of benzene. 3.05 g (11.5 mmol) of 2-tert-butoxy-4,4-bis (trifluoromethyl)-1,3-oxazabuta-1,3-diene in 10 mL of benzene were added dropwise to this solution at room temperature. The reaction solution was heated overnight to 60° C. and benzene was then removed in vacuo. The residue was chromatographed over silica gel (eluent: petroleum ether/ethyl acetate=8/1). Yield: 3.7 g (78%). Melting point: 76–77° C. [α]$^{20}$=−28° (c=1, CHCl$_3$).

18e) (S)-2-(4,4-Bis(trifluoromethyl)-2,5-dioxoimidazolidin-1-yl)-2-(cyclopropylmethyl)acetic acid A solution of 7 g (17.3 mmol) of the compound of Example 18d in 20 mL of dichloromethane was added at 10° C. to a mixture of 30 mL of trifluoroacetic acid and 50 mL of dichloromethane and the mixture was stirred at room temperature for 16 hours. After removal of trifluoroacetic acid and dichloromethane in vacuo, 5.9 g (98%) of the title compound were obtained.

Melting point: 123–125° C., [α]$^{22}$=−26° (c=2, methanol).
18f) (S)-2-(4,4-Bis(trifluoromethyl)-3-(4-(3-(2-methylphenyl)ureido)-3-methoxybenzyl)-2,5-dioxoimidazolidin-1-yl)-2-(cyclopropylmethyl)acetic Acid

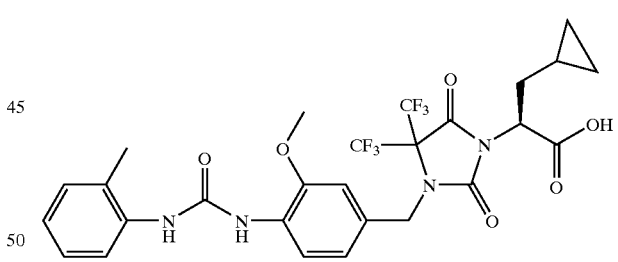

3.2 mL of an n-butyllithium solution (2.5 M in hexane) were added at −40° C. under argon to a solution of 1.39 g (4 mmol) of the compound of Example 18e in 40 mL of absolute THF. The reaction mixture was allowed to warm to 0° C. with stirring, a solution of 2.43 g (8 mmol) of 4-(3-(2-methylphenyl)ureido)-3-methoxybenzyl chloride in 20 mL of absolute THF was added and the reaction mixture was stirred at room temperature for 3 hours. 20 mL of 1N hydrochloric acid were added and THF was removed in vacuo. The aqueous phase was extracted twice with methyl tert-butyl ether. The combined organic phases were dried over sodium sulfate and, after filtration, concentrated in vacuo. The residue was purified by preparative HPLC. After concentration of the product fractions and freeze drying, 1.41 g (57%) of the title compound were obtained.

18g) (R)-3-((S)-2-(4,4-Bis(trifluoromethyl)-3-(4-(3-(2-methylphenyl)ureido)-3-methoxybenzyl)-2,5-dioxoimidazolidin-1-1)-2-(cyclopropylmethyl)acetylamino)-3-methylpropionic Acid The title compound can be obtained as described in Examples 1f and 1g from the compound of Example 18f and tert-butyl (R)-3-aminobutanoate by coupling and subsequent cleavage of the tert-butyl ester.

Example 19
(S)-3-((S)-2-(4,4-Bis(trifluoromethyl)-3-(4-(3-(2-methylphenyl)ureido)-3-methoxybenzyl)-2,5-dioxoimidazolidin-1-yl)-2-(cyclopropylmethyl)acetylamino)-3-phenylpropionic Acid

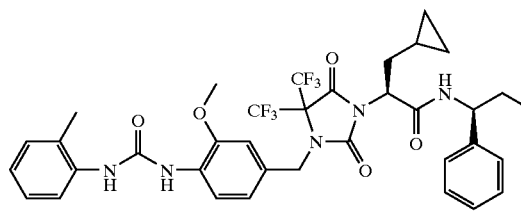

19a) Ethyl (S)-3-((S)-2-(4,4-bis (trifluoromethyl)-3-(4-(3-(2-methylphenyl)ureido)-3-methoxybenzyl)-2,5-dioxoimidazolidin-1-yl)-2-(cyclopropylmethyl)acetylamino)-3-phenylpropionate 748 mg (2.28 mmol) of TOTU (O((cyano(ethoxycarbonyle)methylene)amine)-N,N,N',N'-tetromethyluronium tetrafluoroborate) and 368 μL of N,N-diisopropyl-ethylamine were added at 0° C. to a solution of 1.41 g (2.28 mmol) of the compound of Example 18f and 442 mg (2.28 mmol) of ethyl (S)-3-amino-3-phenylpropionate in 20 mL of absolute dimethylformamide (DMF). After stirring at room temperature for 1 hour, the DMF was removed in vacuo, the residue was taken up in ethyl acetate and the ethyl acetate solution was washed successively with an aqueous $KHSO_4/K_2SO_4$ solution, a saturated $NaHCO_3$ solution and water. After drying the organic phase over sodium sulfate and filtering, the solvent was removed in vacuo and the residue was chromatographed over silica gel using heptane/ethyl acetate (3/2). By concentrating the product fractions, 1.48 g (82%) of the title compound were obtained.

19b) (S)-3-((S)-2-(4,4-Bis(trifluoromethyl)-3-(4-(3-(2-methylphenyl)ureido)-3-methoxybenzyl)-2,5-dioxoimidazolidin-1-yl)-2-(cyclopropylmethyl)acetylamino)-3-phenylpropionic Acid A solution of 1.46 g (1.84 mmol) of the compound of Example 19a in 40 mL of N-methyl-2-pyrrolidone and 20 mL of 6N hydrochloric acid was heated to 60° C. for 6 hours. After cooling to room temperature, the reaction mixture was poured onto 300 mL of water, and the precipitate was filtered off with suction, washed with water and dried over phosphorus pentoxide. The crude product was chromatographed twice over silica gel (eluent: dichloromethane/methanol/acetic acid/water=95/5/0.5/0.5). After concentration of the product fractions, the residue was taken up in dichloromethane and the organic phase was washed with water and dried over sodium sulfate. After filtration, removal of the solvent in vacuo and freeze drying, 1.19 g (85%) of the title compound were obtained.

ES(+)-MS: 764.2 (M+H)$^+$

Example 20
(R)-3-((S)-2-(4,4-Bis(trifluoromethyl)-3-(4-(3-(2-methylphenyl)ureido)-3-methoxybenzyl)-2,5-dioxoimidazolidin-1-yl-2-(2-methylpropyl)acetylamino)-3-methylpropionic Acid

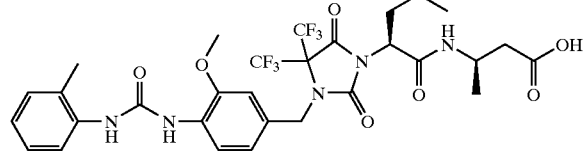

20a) N-Formyl-L-leucine tert-butyl Ester

The preparation was carried out analogously to W. Duczek et al., Synthesis, 37–38 (1996). A solution of 4.04 g (40 mmol) of triethylamine in 10 mL of dichloromethane was added at 0° C. to a solution of 8.94 g (40 mmol) of L-leucine tert-butyl ester hydrochloride and 3.4 g (40 mmol) of cyanomethyl formate in 60 mL of dichloromethane. The reaction solution was allowed to warm to room temperature, stirred overnight at room temperature and then washed twice with saturated NaCl solution. The phases were separated and the organic phase was dried over magnesium sulfate. After filtration and removal of the solvent in vacuo, the residue obtained was distilled in vacuo. Yield: 7.5 g (87%). Boiling point: 118° C./2.7 Pa (0.02 torr).

20b) tert-Butyl (S)-2-(4,4-bis(trifluoromethyl)-2,5-dioxoimidazolidin-1-yl)-2-(2-methylpropyl)acetate 2.4 g (12.1 mmol) of diphosgene were added at –30° C. to a solution of 2.5 g (11.6 mmol) of N-formyl-L-leucine tert-butyl ester and 2.5 g (24.7 mmol) of triethylamine in 100 mL of dry dichloromethane. The reaction solution was allowed to warm to –10° C. in the course of 1 hour and stirring was continued at this temperature until the reaction was complete. The reaction solution was then washed twice at room temperature with 7% strength sodium hydrogencarbonate solution. The phases were separated and the organic phase was dried over magnesium sulfate. After filtration, the solvent was removed in vacuo and the residue was taken up in 70 mL of benzene. 3 g (11.3 mmol) of 2-tert-butoxy-4,4-bis(trifluoromethyl)-1,3-oxazabuta-1,3-diene in 10 mL of benzene were added dropwise to this solution at room temperature. The reaction solution was heated to 60° C. overnight and then benzene was removed in vacuo. After chromatography of the residue over silica gel (eluent: petroleum ether/ethyl acetate 10/1), 3.7 g (80%) of the title compound were obtained. Melting point: 105–106° C. $[\alpha]^{20}$=–24° (c=1, $CHCl_3$).

20c) (S)-2-(4,4-Bis(trifluoromethyl)-2,5-dioxoimidazolidin-1-yl)-2-(2-methylpropyl)acetic Acid A solution of 7 g (17.2 mmol) of the compound of Example 20b in 20 mL of dichloromethane was added at 10° C. to a mixture of 30 mL of trifluoroacetic acid and 50 mL of dichloromethane and the reaction mixture was stirred at room temperature for 16 hours. After removal of trifluoroacetic acid and dichloromethane in vacuo, 6.0 g (99%) of the title compound were obtained. Melting point: 154–156° C. $[\alpha]^{22}$ =–23° (c=2, methanol).

20d) (R)-3-((S)-2-(4,4-Bis(trifluoromethyl)-3-(4-(3-(2-methylphenyl)ureido)-3-methoxy-benzyl)-2,5-dioxoimidazolidin-1-yl)-2-(2-methylpropyl) acetylamino)-3-methylpropionic Acid The title compound was prepared as described in Examples 1f and 1g from 500 mg (0.809 mmol) of (S)-2-(4,4-bis(trifluoromethyl)-3-(4-(3-(2-methylphenyl)ureido)-

3-methoxybenzyl)-2,5-dioxoimidazolidin-1-yl)-2-(2-methylpropyl)acetic acid of the formula

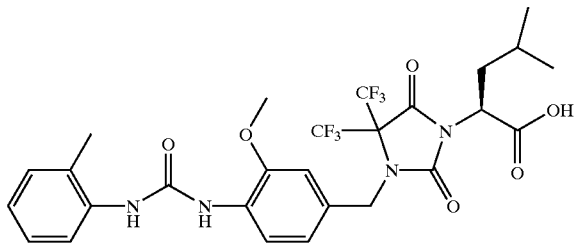

which had been prepared from (S)-2-(4,4-bis(trifluoromethyl)-2,5-dioxoimidazolidin-1-yl)-2-(2-methylpropyl)acetic acid and 4-(3-(2-methylphenyl)ureido)-3-methoxybenzyl chloride as described in Example 18f, and 128 mg (0.809 mmol) of tert-butyl (R)-3-aminobutanoate. After coupling, chromatographic purification over silica gel (eluent: heptane/ethyl acetate=3/2) and cleavage of the tert-butyl ester, 299 mg (53%) of the title compound were obtained.

ES(+)-MS: 704.5 (M+H)+

Example 21
(S)-3-((S)-2-(4,4-Bis(trifluoromethyl)-3-(4-(3-(2-methylphenyl ureido)-3-methoxybenzyl)-2,5-dioxoimidazolidin-1 yl)-2-(2-methylpropyl)acetylamino)-3-phenylpropionic Acid

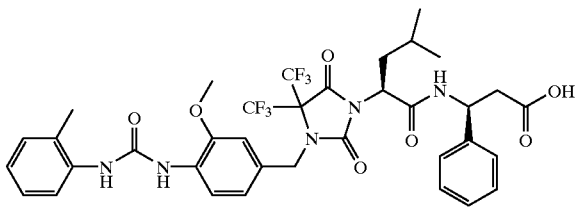

21a) Ethyl (S)-3-((S)-2-(4,4-bis(trifluoromethyl)-3-(4-(3-(2-methylphenyl)ureido)-3-methoxybenzyl)-2,5-dioxoimidazolidin-1-yl)-2-(2-methylpropyl)acetylamino)-3-phenylpropionate 1.89 g (5.77 mmol) of TOTU and 932 µL of N,N-diisopropylethylamine were added at 0° C. to a solution of 3.57 g (5.77 mmol) of (S)-2-(4,4-bis(trifluoromethyl)-3-(4-(3-(2-methylphenyl)ureido)-3-methoxybenzyl)-2,5-dioxoimidazolidin-1-yl)-2-(2-methylpropyl)acetic acid (prepared from (S)-2-(4,4-bis(trifluoromethyl)-2,5-dioxoimidazolidin-1-yl)-2-(2-methylpropyl)acetic acid and 4-(3-(2-methylphenyl)ureido)-3-methoxybenzyl chloride as described in Example 18f) and 1.11 g (5.77 mmol) of ethyl (S)-3-amino-3-phenylpropionate in 30 mL of absolute DMF. After stirring at room temperature for 1 hour, DMF was removed in vacuo, the residue was taken up in ethyl acetate and the ethyl acetate solution was washed successively with an aqueous KHSO4K2SO4 solution, a saturated NaHCO3 solution and water. After drying the organic phase over sodium sulfate and filtering, the solvent was removed in vacuo and the residue was chromatographed over silica gel using ethyl acetate/heptane (2/3). After concentration of the product fractions, 3.26 g (71%) of the title compound were obtained.

21b) (S)-3-((S)-2-(4,4-Bis(trifluoromethyl-3-(4-(3-(2-methylphenyl)ureido)-3-methoxybenzyl)-2,5-dioxoimidazolidin-1-yl)-2-(2-methylpropyl)acetylamino)-3-phenylpropionic acid 45 mL of 6N hydrochloric acid were added to a solution of 3.25 g (4.09 mmol) of the compound of Example 21a in 90 mL of N-methyl-2-pyrrolidone and the mixture was heated to 60° C. for 6 hours. After cooling to room temperature, the mixture was poured onto 600 mL of water. The precipitate was filtered off with suction, washed with water and dried over phosphorus pentoxide. After twofold chromatographic purification of the crude product over silica gel (eluent: dichloromethane/methanol/acetic acid/water= 95/5/0.5/0.5) and concentration of the product fractions, the residue was taken up in dichloromethane. The organic phase was washed twice with water and dried over magnesium sulfate. After filtration, concentration and freeze drying, 2.7 g (86%) of the title compound were obtained.

ES(+)-MS: 766.2 (M+H)+

Example 22
(S)-3-((S)-2-(4,4-Bis(trifluoromethyl)-3-(4-(3-(2-methylphenyl)ureido)-3-methoxybenzyl)-2,5-dioxoimidazolidin-1-yl)-2-(2-methylpropyl)acetylamino)-3-phenylpropionic Acid Sodium Salt

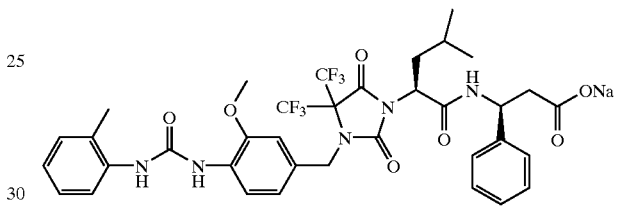

1.24 mL of 1N sodium hydroxide solution (diluted with 20 mL of water) were added with stirring to a suspension of 1 g (1.3 mmol) of the compound of Example 21 in 100 mL of acetonitrile and 200 mL of water. After freeze drying the solution, 1.01 g (79%) of the title compound were obtained.

ES(+)-MS: 766.2
(3-((S)-2-(4,4-bis(trifluoromethyl)-3-(4-(3-(2-methylphenyl)ureido)-3-methoxybenzyl)-2,5-dioxoimidazolidin-1-yl)-2-(2-methylpropyl)acetylamino)-3-phenylpropionic acid+H)+

Example 23
(S)-3-((S)-2-(4,4-Bis(trifluoromethyl)-3-(4-(3-(2-methylphenyl)ureido)-3-methoxybenzyl)-2,5-dioxoimidazolidin-1-yl-2-(cyclopropylmethyl)acetylamino)-3-phenylpropionic Acid Sodium Salt

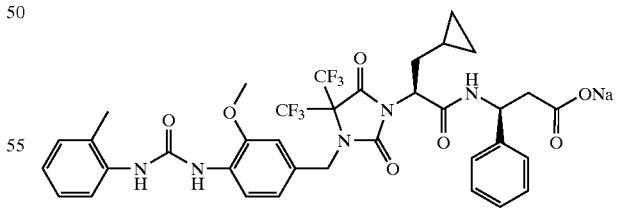

From 720 mg of the compound of Example 19b, according to the process described in Example 22, 720 mg (99%) of the title compound were obtained.

ES(+)-MS: 764.3
((S)-3-((S)-2-(4,4-bis(trifluoromethyl)-3-(4-(3-(2-methylphenyl)ureido)-3-methoxybenzyl)-2,5-dioxoimidazolidin-1-yl)-2-(cyclopropylmethyl)acetylamino)-3-phenylpropionic acid+H)+

Investigation of the Biological Activity
A) U937/VCAM-1 Cell Adhesion Test

The test method used for the activity of the compounds of formula I on the interaction between VCAM-1 and VLA-4 is the assay described below, which is specific for this interaction. The cellular binding components, i.e., the VLA-4 integrins, are supplied in their natural form as surface molecules on human U937 cells (ATCC CRL 1593), which belong to the leukocytes group. As specific binding components, recombinant soluble fusion proteins prepared by genetic engineering, consisting of the extracytoplasmic domain of human VCAM-1 and the constant region of a human immunoglobulin of subclass IgG1, are used.

Assay for the measurement of the adhesion of U937 cells (ATCC CRL 1593) to hVCAM-1(1-3)-IgG 1. Preparation of Human VCAM-1(1-3)-IgG and Human CD4-IgG A genetic construct for the expression of the extracellular domain of human VCAM-1, combined with the genetic sequence of the heavy chain of the human immunoglobulin IgG1 (hinge, CH2 and CH3 regions) (from Dr. Brian Seed, Massachusetts General Hospital, Boston, USA; cf. Damle and Aruffo, *Proc. Natl. Acad. Sci. USA*, 88:6403 (1991)), was employed. The soluble fusion protein hVCAM-1(1-3)-IgG contained the three amino-terminal extracellular immunoglobulin-like domains of human VCAM-1 (Damle and Aruffo, *Proc. Natl. Acad. Sci. USA*, 88:6403 (1991)). CD4-IgG (Zettlmeissl et al., *DNA and Cell Biology*, 9:347 (1990)) served as a fusion protein for negative controls. The recombinant proteins were expressed as soluble proteins after DEAE/dextran-mediated DNA transfection in COS cells (ATCC CRL1651) according to standard procedures (Ausubel et al., "Current Protocols in Molecular Biology", John Wiley & Sons, Inc., 1994).

2. Assay for the Measurement of the Adhesion of U937 Cells to hVCAM-1 (1-3)-IgG 2.1 96 well microtiter test plates (Nunc Maxisorb) were incubated at room temperature for 1 hour with 100 µL/well of a goat anti-human IgG antibody solution (10 µg/mL in 50 mM tris, pH 9.5). After removal of the antibody solution, washing was carried out once with PBS.

2.2 150 µL/well of a blocking buffer (1% BSA in PBS) were incubated on the plates at room temperature for 0.5 hour. After removal of the blocking buffer, washing was carried out once with PBS.

2.3 100 µL per well of a cell culture supernatant of transfected COS cells were incubated on the plates at room temperature for 1.5 hours. The COS cells were transfected with a plasmid which codes for the three N-terminal immunglobulin-like domains of VCAM-1, coupled to the Fc part of human IgG1 (hVCAM-l(1-3)-IgG). The content of hVCAM-1(1-3)-IgG was about 0.5–1 µg/mL. After removal of the culture supernatant, washing was carried out once with PBS.

2.4 The plates were incubated at room temperature for 20 minutes with 100 µL/well of Fc receptor block buffer (1 mg/mL γ-globulin, 100 mM NaCl, 100 µM $MgCl_2$, 100 µM $MnCl_2$, 100 µM $CaCl_2$, 1 mg/mL BSA in 50 mM HEPES, pH 7.5). After removal of the Fc receptor block buffer, washing was carried out once with PBS.

2.5 20 µL of binding buffer (100 mM NaCl, 100 µM $MgCl_2$, 100 µM $MnCl_2$, 100 µM $CaCl_2$, 1 mg/mL BSA in 50 mM HEPES, pH 7.5) were introduced, the substances to be tested were added in 10 µL of binding buffer and incubation was carried out for 20 minutes. Antibodies against VCAM-1 (BBT, No. BBA6) and against VLA-4 (Immunotech, No. 0764) served as controls.

2.6 U937 cells were incubated for 20 minutes in Fc receptor block buffer and then added by pipette in a concentration of $1 \times 10^6$/mL and in an amount of 100 µL per well (final volume 125 µL/well).

2.7 The plates were slowly immersed at an angle of 45° in stop buffer (100 mM NaCl, 100 µM $MgCl_2$, 100 PM $MnCl_2$, 100 µM $CaCl_2$ in 25 mM tris, pH 7.5) and shaken off. The process was repeated.

2.8 50 µL/well of a dye solution (16.7 µg/mL of Hoechst dye 33258, 4% formaldehyde, 0.5% Triton X-100 in PBS) were then incubated on the plates for 15 minutes.

2.9 The plates were shaken out and slowly immersed at an angle of 45° in stop buffer (100 mM NaCl, 100 µM $MgCl_2$, 100 µM $MnCl_2$, 100 µM $CaCl_2$ in 25 mM tris, pH 7.5). The process was repeated. Then, with the liquid (stop buffer) present, the plates were measured in a cytofluorimeter (Millipore) (sensitivity: 5, filter: excitation wavelength: 360 nm, emission wavelength: 460 nm).

The intensity of the light emitted by the stained U937 cells is a measure of the number of the U937 cells adhered to the hVCAM-1(1-3)-IgG and remaining on the plate and thus a measure of the ability of the added test substance to inhibit this adhesion. From the inhibition of the adhesion at various concentrations of the test substance, the concentration $IC_{50}$ was calculated which leads to an inhibition of the adhesion by 50%.

3. Results

The following results were obtained in the U937/VCAM-1 cell adhesion test ($IC_{50}$ values in nM (nanomoles/liter)).

| Compound Example No. | of $IC_{50}$ (nM) |
| --- | --- |
| 1 | 0.3 |
| 2 | 0.5 |
| 5 | 25.9 |
| 7 | 2.1 |
| 10 | 0.6 |
| 13 | 1.8 |
| 16 | 0.9 |
| 19 | 4.4 |

The pharmacological properties of the compounds of formula I also can be investigated in the following models.

B) Leukocyte Adhesion in the Rat

In the model of leukocyte adhesion in the rat, the influencing of the adhesion of leukocytes by the compounds of formula I is investigated in venules of the rat. The leukocyte adhesion to the endothelium of postcapillary venules is regarded as an important step in inflammatory reactions (J. M. Harlan, *Blood*, 65:513 (1985)). In the recruitment of leukocytes from the blood into inflamed areas a well-coordinated dynamic sequence of events takes place, wherein chemotactic cytokines and cellular adhesion molecules play an active role. It has been found that VCAM-1/VLA-4 interactions play a crucial role in the adhesion and emigration of leukocytes and the increased permeability of vessels for macromolecules which are induced by various mediator substances and cytokines (D. Seiffge, *Int. J. Microcirc.*, 15:301 (1995)). In the present model, a generalized inflammation or rheumatoid arthritis which leads to an adhesion of the leukocytes and their emigration into diseased areas of the organ is caused by local or systemic injection of endotoxins, for example zymosan, bacterial toxins such as lipopolysaccharides (LPS) or Freund's adjuvant. The increased adhesion to the endothelium of the venules produced by the endotoxin is determined.

For the determination of the leukocyte adhesion, a camera inverted microscope (Zeiss) is used which is equipped with a video system. Zymosan or bacterial endotoxin is injected into male Sprague-Dawley rats (body weight about 250 g) under a light halothane premedication. The control animals receive an identical volume of 0.9% strength saline solution. The test substance then is administered subcutaneously or orally to the animals as an individual dose or as a multiple dose. For carrying out the measurement, the rats are anesthetized by an intramuscular injection of 1.25 g/kg of urethane. They are allowed to breathe spontaneously through a tracheal tube. The body temperature is kept at 37° C. by means of a regulated heating pat. On a thermostatted (37° C.) window of the microscope stage, the mesentery is carefully exposed by means of a hypogastric incision and covered with liquid paraffin at 37° C. The ileocecal area of the mesentery is held in position using three blunt needles and modeling clay. After a 30-minute equilibration period, during which the tissue is allowed to stabilize, the leukocyte adhesion is determined in postcapillary venules of 20–30 µm diameter and about 100 µm length by counting in 2–3 segments of the venules at intervals of 10 minutes for 1 hour. A leukocyte is regarded as being adherent to the endothelium if it is stationary for more than 30 seconds. After the experiment, the systemic leukocyte count and the fibrinogen content of the blood are determined. The inhibition of the leukocyte adhesion by the test substance is indicated by the decrease (in %) in the number of adherent leukocytes in the treated animals in comparison with the number in the control animals.

C) Delayed-Type Hypersensitivity in the Mouse

In the model of delayed-type hypersensitivity (DTH), the antiallergic or anti-inflammatory action of the compounds of formula I is investigated. DTH is an inflammatory reaction of the skin which is induced by sensitization with antigenic substances. In order to determine the corresponding inflammatory reaction and the leukocyte recruitment into the inflamed areas in vivo, the substances are tested in the following DTH model in the mouse (see also T. B. Issekutz, J. Immunol., 147:4178 (1991)).

Groups of female BALB/c mice (body weight about 20 g) are sensitized epicutaneously on a shaved part of the skin with 150 µL of a 3% strength solution of oxazalone, which induces a strong inflammatory DTH reaction. 6 days later, the reaction is challenged by administration of 20 µL of a 1% strength oxazalone solution to the right ear of the animals. The test substances are administered subcutaneously or orally in each case 44 hours before the challenge of the reaction, 20 hours before the challenge and 4 hours after the challenge. Directly before the challenge of the reaction and 24 hours after the challenge, the altered ear thickness due to the inflammatory swelling of the ear is measured on the right ear using a Mitutoyo Engineering micrometer. The difference between these two measurements is determined for each animal of the group. The mean values of the differences of an animal group treated with the test substance on the one hand and an untreated control group on the other hand are compared. As a measure of the effect of the substance, the percentage inhibition of the ear swelling is indicated.

D) Antiasthmatic Action on the Guinea Pig

The effect on the lung function and the antiasthmatic action of the compounds of formula I can be determined in a model on the guinea pig which follows the method described by G. Moacevic, Arch. Toxicol., 34:1 (1975). For this, the technical preparations for the investigation are carried out according to the details described by Moacevic. Male albino guinea pigs having a body weight of 300–500 g are employed. The animals are placed in a plethysmograph (from FMI) and three starting values of the parameters respiratory rate and respiratory amplitude are recorded. In this model, asthmatic respiration is characterized by the decrease in the respiratory amplitude (=lowering of the respiratory volume on account of the bronchoconstriction) and the increase in the respiratory rate (=reflex reaction). This condition is known in asthma patients as dyspnea.

The albino guinea pigs are sensitized 22 days before the start of the study with 1 mL per animal of a 0.1% strength ovalbumin solution on two successive days. The experimental asthma attack is induced by inhalation of a 0.3% strength ovalbumin solution for 1 minute. After a recovery phase of 40–60 minutes, the animals inhale the test substance as an aqueous solution. Immediately thereafter, 0.3% strength ovalbumin solution is administered for 1 minute. In the following recovery phase of 30 minutes, the animals breathe normal air. This process is repeated twice. If the asthma attacks are life threatening, oxygen is administered to the animals.

The antiasthmatic effect on the sheep can be determined, for example, as described by Abraham et al., J. Clin. Invest., 93:776 (1994).

E) The Antiatherosclerotic Action can be Investigated in the Following Animal Models.

Cuff Model of Neointima Formation

The wild-type mice of the strain C57BL/6J are supplied by the breeding service of Charles River Wiga GmbH (Sulzfeld, FRG) and the homozygous KO mice of the strain C57BL/6J-ApoE tm1Unc (ApoE KO) are supplied by The Jackson Laboratory (Maine, USA). All mice are between 10 and 12 weeks old at the start of the experiment and are kept in fully air-conditioned rooms at a temperature of 22° C. The day/night phase of the controlled light program is adjusted to a period of 12 hours. The mice are firstly anesthetized with 60 mg/kg of body weight of pentobarbital sodium i.p. Each animal then additionally receives 0.01 mg/10 g of body weight of xylazine i.m.

The mice are fixed in the supine position, and the inner surfaces of both hind legs are shaved and disinfected. The skin on the inside of the left thigh then is opened by means of a longitudinal incision approximately 1 cm long and the femoral artery is isolated from the surrounding tissue and from the femoral vein and the sciatic nerve. A piece of polyethylene tubing approximately 2 mm long (internal diameter 0.58 mm, external diameter 0.965 mm, Becton Dickinson, Sparks, Md., USA) then is cut according to length and placed around the femoral artery and fixed with Prolene threads (7/0, 0.5 metric from Ethicon, Norderstedt, FRG). The skin is subsequently closed again by means of a continuous suture. The right hind leg is operated on in an analogous manner, but without a cuff being placed around the femoral artery. The animal is subsequently taken to its cage again. From the operation, the animals are treated daily with the test substance.

At the end of the experiment, the mice are again anesthetized with 60 mg/kg of body weight of pentobarbital sodium i.p. and 0.01 mg/10 g of body weight of xylazine i.m. For the fixation of the vessels in situ, each mouse then receives an injection of 4% strength formalin solution into the abdominal aorta. The right and the left femoral arteries are then removed. On the left side, the portion of the artery is removed which includes the section about 1 mm proximal to the cuff, the section enclosed by the cuff itself and the section of vessel 1 mm distal. On the right side, this portion corresponds to the section which is only isolated during the operation, but not enclosed by a cuff.

The portions of the left and the right femoral arteries fixed in 4% strength formalin solution are embedded in paraffin. From the section of the left artery enclosed by the cuff and from the corresponding section of the right control artery a number of tissue cross sections are prepared which are then stained with hematoxylin and eosin for software-assisted (LeicaQWin from Leica Imaging Systems, Cambridge, GB) morphometric analysis.

Per mouse, three tissue cross sections from the area of the left femoral artery enclosed by the cuff and three tissue cross sections from the corresponding area of the right control artery are evaluated. After marking of the lamina elastica externa, the lamina elastica interna and the boundary between the lumen and endothelium, the following areas are calculated by the analysis program: lumen, neointima and media. The size of these areas is indicated in the unit $\mu m^2$. The effect of a compound is indicated by the reduction of the ratio of neointima/media in comparison with the control group.

Heart Transplantation

In the model of allogenic heart transplantation, transplantations between two genetically incompatible rat strains are carried out. For this purpose, Wistar-Furth rats are used as donor animals and Lewis rats as recipient animals. The animals are obtained from the breeding service of Charles River Wiga GmbH (Sulzfeld, FRG). Male Lewis rats of 270–330 g aged 2.5 to 3 months, and male Wistar-Furth rats of 200–250 g aged from 1.5 to 2 months are kept under constant, controlled conditions (temperature 19–22° C.; relative humidity 50–55%; the day/night phase of the controlled light program is adjusted to a period of 12 hours).

For the operation, the rats receive a combination of 3.3 mg/kg of body weight of xylazine and 115 mg/kg of body weight of ketamine. After the onset of the anesthetic action, the abdomen of the recipient is opened by median incision. The abdominal aorta and inferior vena cava are separated from one another between the renal artery and vein and the iliolumbal vessels. The aorta then is closed cranially using a vessel clip. Caudally, a silk thread is placed around both vessels and tightened. A second silk thread lies loosely around the cranial end of the inferior vena cava. After opening the abdominal cavity, the donor animal is killed by cutting through the large abdominal vessels. This point in time signaled the start of the ischaemic period of the donor organ. The diaphragm then is opened and the heart is exposed. The superior and inferior vena cava are ligated and cut through on the side of the ligature distal to the heart. A mass ligature of the pulmonary veins is carried out using a silk thread. The aorta and pulmonary artery are then lifted with forceps and cut through. The transplant then is freed of blood residues in the vascular system. The heart then is lifted, removed together with the mass ligature from the lung and stored in cold physiological NaCl solution for one to two minutes. An end-to-side anastomosis of the aorta and of the pulmonary artery of the donor organ with the abdominal artery and inferior vena cava respectively of the recipient animal then is carried out. After completion of the vessel anastomoses, the venous circulation followed by the arterial circulation are successively released. Finally, the abdominal cavity is closed again using a peritoneum/muscle suture and a skin suture. After release of the blood circulation and a short recovery phase, the transplanted heart beats with a sinus rate of about 100 to 120 beats/minute. Cyclosporin A(CSA) for immunosuppression is administered either subcutaneously (s.c.) or orally via the drinking water. After getting over the acute rejection period, the dose can be reduced from 25 mg/kg of body weight from the 15th day p.op. to 5 mg/kg of body weight. The injections are performed once daily in the morning in the neck area of the animals.

The changeover from s.c. CSA administration to oral CSA administration takes place on day 22 p.op. in order to have safely got over the acute rejection period. The substance to be investigated is administered for 100 days from the operation. After expiration of the observation time interval (100 days), the animals are anesthetized and the abdominal cavity is opened. The heart then is removed with protection of the vessel stumps of the abdominal vessels, cut into slices and in stored in 4% formalin solution. After the heart slices have been fixed, these are embedded in paraffin and stained for elastica according to the standardized van Gieson histological technique. The classification of the neointimal proliferation and the constriction of the vascular lumen associated therewith is performed according to Adams et al., *Transplantation*, 56:794 (1993). Adhesions between the lamina elastica interna and endothelium are classified. The special stain according to van Gieson which selectively emphasizes elastica fibers facilitates the assessment. The effect of a compound is indicated by the reduction of the neointimal proliferation and thus the transplant atherosclerosis in comparison with the control group.

Atherosclerosis Model in ApoE Knockout (KO) Mice

The homozygous KO mice of the strain C57BL/6J-ApoE tm1Unc (ApoE KO) are supplied by The Jackson Laboratory (Maine, USA). All mice are between 10 and 12 weeks old at the start of the experiment and are kept on standard litter for laboratory animals (Altromin, Lage, FRG) in fully air-conditioned rooms at a temperature of 22° C. The day/night phase of the controlled light program is adjusted to a period of 12 hours. The animals are treated with the test substance for 4 months.

At the end of the experiment, the mice are anesthetized with 60 mg/kg of body weight of pentobarbital sodium i.p. and 0.01 mg/10 g of body weight of xylazine i.m. The heart and aortic arch and the descending thoracic aorta are then removed and fixed in 4% strength formalin solution. The descending aorta is treated with Oil Red O for the staining of fat lesions. The morphometric analysis of the fat lesions is carried out using a microscope (Leitz DM RBE type from Leica, Bensheim), a camera attached thereto having a control unit (CF 15 MCC Type, Kappa Meetechnik, Gleichen) and a computer (Leica, Bensheim). The measurements are carried out with the aid of a computer program for image analysis (LeicaQWin from Leica Imaging Systems, Cambridge, GB). The heart and the aortic arch are cut longitudinally and stained with hematoxylin and eosin for morphometric analysis. In each case 15–20 sections are analyzed. Further sections are investigated immunohistochemically for macrophages and T lymphocytes. The effect of a compound is indicated by the reduction of the plaque formation in the aorta in comparison with the control group.

F) The Cardioprotective Action can be Investigated for Example in the Following Animal Model.

Cardiac Infarct Size in the Rat

Male Wistar rats are obtained from the breeding service of Charles River Wiga GmbH (Sulzfeld, FRG) at an age of 2.5 to 3 months and having a body weight of 270–330 g. The animals are kept under constant, controlled conditions (temperature 19–22° C.; relative humidity 50–55%; the day/night phase of the controlled light program is adjusted to a period of 12 hours). For the operation, the rats receive a combination of 3.3 mg/kg of body weight of xylazine and 115 mg/kg of body weight of ketamine. The animals are then intubated and ventilated with 30% oxygen. The thorax is shaved, disinfected and opened by means of a left lateral thoracotomy. The left coronary artery is permanently ligated 2–3 mm below the left auricle of the heart for 48 hours or 4 weeks, or it is ligated for 30 minutes and reperfused for 47.5 hours or 4 weeks.

After the operation, the thorax is closed again and the animals are extubated after commencing spontaneous respiration. The test substance is administered 30 minutes after the ligature or immediately before the reperfusion. The animals are then treated daily with the test substance. At the end of the experiment, the animals are again anesthetized with a combination of 3.3 mg/kg of body weight of xylazine and 115 mg/kg of body weight of ketamine. For the wall motion analysis, the animals in which the hearts were reperfused are investigated by means of "Nuclear Magnetic Resonance Imaging". In animals with nonreperfused hearts, a tip catheter is introduced via the right carotid artery for the measurement of the ventricular pressure and the contractility in the left heart chamber. The heart then is removed in all animals and perfused in a retrograde manner in a Langendorff apparatus via the aorta with warm 1% strength Evans Blue solution at 37° C. for the determination of the anatomical risk area and of the nonischemic area. The hearts are then cut into 5–6 thin slices and incubated in 2,3,5-triphenyltetrazolium chloride solution for 15 minutes for the determination of the vital and of the dead heart tissue. The planimetric analysis of the risk area and of the infarct region is carried out using a camera (Leica, Bensheim) and an attached computer unit with analysis software (Leitz, Bensheim). The risk area is expressed in percent based on the left ventricle plus septum and the infarct region in percent based on the risk area. The effect of a compound is indicated by the reduction of the infarct region based on the risk area in comparison with the control group.

What is claimed is:

1. A compound of formula I,

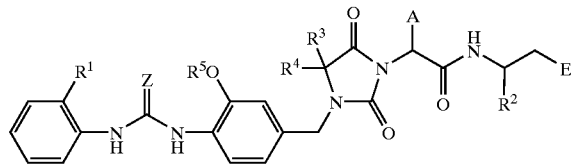

wherein
A is cyclopropylmethyl- or isobutyl;
E is —CO—$R^6$, —CO—H or —$CH_2$—O—$R^7$;
Z is oxygen or sulfur;
$R^1$ is hydrogen or methyl;
$R^2$ is phenyl, pyridyl or ($C_1$–$C_4$)-alkyl, where the alkyl residue can be substituted by one or more fluorine atoms and the phenyl residue can be substituted by one or more identical or different substituents selected from the group consisting of ($C_1$–$C_4$)-alkyl, ($C_1$–$C_4$)-alkoxy, methylenedioxy, ethylenedioxy, halogen, trifluoromethyl and trifluoromethoxy;
$R^3$ and $R^4$ are methyl or trifluoromethyl;
$R^5$ is hydrogen or ($C_1$–$C_4$)-alkyl, where the alkyl residue can be substituted by one or more fluorine atoms;
$R^6$ is hydroxyl, ($C_1$–$C_{10}$)-alkoxy, phenyl-($C_1$–$C_8$)-alkoxy, phenyloxy, ($C_1$–$C_8$)-alkylcarbonyloxy-($C_1$–$C_6$)-alkoxy, phenylcarbonyloxy-($C_1$–$C_6$)-alkoxy, phenyl-($C_1$–$C_6$)-alkylcarbonyloxy-($C_1$–$C_6$)-alkoxy, ($C_1$–$C_8$)-alkoxycarbonyloxy-($C_1$–$C_6$)-alkoxy, phenyloxycarbonyloxy-($C_1$–$C_6$)-alkoxy, phenyl-($C_1$–$C_6$)-alkoxycarbonyloxy-($C_1$–$C_6$)-alkoxy, amino, mono(($C_1$–$C_{10}$)-alkyl)amino or di(($C_1$–$C_{10}$)-alkyl)amino;
$R^7$ is hydrogen or ($C_1$–$C_4$)-alkyl;
in all its stereoisomeric forms and mixtures thereof in all ratios,
or its physiologically acceptable salts.

2. The compound as claimed in claim 1, wherein $R^3$ and $R^4$ are both methyl or trifluoromethyl.

3. The compound as claimed in claim 1, wherein Z is oxygen.

4. The compound as claimed in claim 1, wherein $R^1$ is methyl and $R^5$ is methyl.

5. The compound as claimed in claim 1, wherein $R^2$ is pyridyl, unsubstituted phenyl, phenyl which is substituted by a methylenedioxy residue or an ethylenedioxy residue, phenyl which is substituted by one or two ($C_1$–$C_4$)-alkoxy groups, or ($C_1$–$C_4$)-alkyl which can be substituted by one or more fluorine atoms.

6. The compound as claimed claim 1, wherein E is —CO—$R^6$ or —$CH_2$—OH and $R^6$ is hydroxyl, ($C_1$–$C_6$)-alkoxy or amino.

7. The compound as claimed in claim 1,
wherein
A is cyclopropylmethyl- or isobutyl;
E is —COOH, —$COOC_2H_5$, —$COOiC_3H_7$ or —$CH_2$—OH;
Z is oxygen;
$R^1$ is methyl;
$R^2$ is unsubstituted phenyl, pyridyl or methyl;
$R^3$ and $R^4$ are methyl;
$R^5$ is methyl.

8. The compound as claimed in claim 1,
wherein
A is cyclopropylmethyl- or isobutyl;
E is —COOH, —$COOC_2H_5$, —$COOiC_3H_7$ or —$CH_2$—OH;
Z is oxygen;
$R^1$ is methyl;
$R^2$ is unsubstituted phenyl, pyridyl or methyl;
$R^3$ and $R^4$ are trifluoromethyl;
$R^5$ is methyl.

9. A process for the preparation of a compound as claimed in claim 1, which comprises reacting a compound of formula II with a compound of formula III

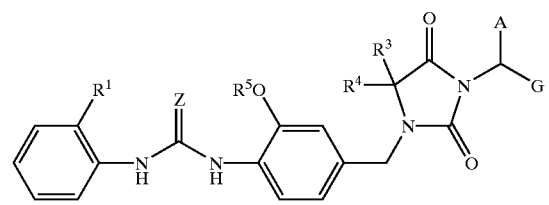

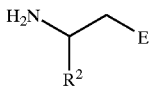

III where A, E, Z, R¹, R², R³, R⁴ and R⁵ are as defined in claim 1 or functional groups are present in protected form or in the form of precursors, and where G is hydroxycarbonyl, $(C_1–C_6)$-alkoxycarbonyl or activated carboxylic acid derivatives.

10. A pharmaceutical composition, which comprises one or more compounds as claimed in claim 1 and/or their physiologically acceptable salts and a pharmaceutical acceptable carrier.

11. A method of treating inflammation comprising administering to a mammal in need thereof an effective amount of a compound as claimed in claim 1 or a pharmaceutically acceptable salt thereof.

12. A method of treating arthritis, rheumatoid arthritis, polyarthritis, inflammatory bowel disease, systemic lupus erythematosus, multiple sclerosis or inflammatory diseases of the central nervous system comprising administering to a mammal in need thereof an effective amount of a compound as claimed in claim 1 or a pharmaceutically acceptable salt thereof.

13. A method of treating asthma or allergies comprising administering to a mammal in need thereof an effective amount of a compound as claimed in claim 1 or a pharmaceutically acceptable salt thereof.

14. A method of treating cardiovascular diseases, atherosclerosis, myocardial infarct, the acute coronary syndrome, stroke, restenoses, diabetes, damage to organ transplants, immune diseases, autoimmune diseases, tumor growth, tumor metastasis, or malaria comprising administering to a mammal in need thereof an effective amount of a compound as claimed in claim 1 or a pharmaceutically acceptable salt thereof.

15. A method for cardioprotection or secondary prophylaxis of stroke comprising administering to a mammal in need thereof an effective amount of a compound as claimed in claim 1 or a pharmaceutically acceptable salt thereof.

16. A method of inhibiting the adhesion and/or migration of leukocytes comprising administering to a mammal in need thereof an effective amount of a compound as claimed in claim 1 or a pharmaceutically acceptable salt thereof.

17. A method for the inhibition of the VLA-4 receptor comprising administering to a mammal in need thereof an effective amount of a compound as claimed in claim 1 or a pharmaceutically acceptable salt thereof.

* * * * *